US009090539B2

(12) United States Patent
Morgan et al.

(10) Patent No.: US 9,090,539 B2
(45) Date of Patent: Jul. 28, 2015

(54) COMPOUNDS AND METHODS FOR PREPARING SUBSTITUTED 3-(1-AMINO-2-METHYLPENTANE-3-YL)PHENYL COMPOUNDS

(71) Applicant: AMPAC Fine Chemicals LLC, Rancho Cordova, CA (US)

(72) Inventors: Brian Morgan, San Diego, CA (US); Olivier Dapremont, Cameron Park, CA (US); Patrick Berget, Sacramento, CA (US); Ali Suleman, Folsom, CA (US); William Dubay, Folsom, CA (US); Jeffrey D. Butler, Folsom, CA (US)

(73) Assignee: AMPAC Fine Chemicals LLC, Rancho Cordova, CA (US)

( * ) Notice: Subject to any disclaimer, the term of this patent is extended or adjusted under 35 U.S.C. 154(b) by 0 days.

(21) Appl. No.: 13/902,296

(22) Filed: May 24, 2013

(65) Prior Publication Data
US 2014/0350283 A1    Nov. 27, 2014

(51) Int. Cl.
| C07C 253/30 | (2006.01) |
| C07C 255/36 | (2006.01) |
| C07C 255/37 | (2006.01) |
| C07C 213/02 | (2006.01) |
| C07C 215/54 | (2006.01) |

(52) U.S. Cl.
CPC ............ *C07C 253/30* (2013.01); *C07C 213/02* (2013.01); *C07C 215/54* (2013.01); *C07C 255/36* (2013.01); *C07C 255/37* (2013.01); *C07B 2200/07* (2013.01); *C07B 2200/09* (2013.01)

(58) Field of Classification Search
USPC ............ 558/170, 401, 70, 375; 564/170, 383, 564/374, 161, 336; 514/649
See application file for complete search history.

(56) References Cited

U.S. PATENT DOCUMENTS

| 6,248,737 B1 | 6/2001 | Buschmann et al. |
| 2002/0010178 A1 | 1/2002 | Buschmann et al. |
| 2006/0167318 A1 | 7/2006 | Jagusch et al. |
| 2009/0043132 A1 | 2/2009 | Hell et al. |
| 2011/0306793 A1* | 12/2011 | Buschmann et al. ......... 564/375 |
| 2012/0283463 A1* | 11/2012 | Marom et al. ............... 558/170 |

FOREIGN PATENT DOCUMENTS

| WO | 2011067714 A1 | 6/2011 |
| WO | 2011080736 A1 | 7/2011 |
| WO | 2011128784 A2 | 10/2011 |
| WO | 2011157390 A2 | 12/2011 |
| WO | 2012001571 A1 | 1/2012 |
| WO | 2012103799 A1 | 8/2012 |

OTHER PUBLICATIONS

Seux, R. et al. "Decyanation of trisubstituted succinonitriles. Z and E configurations of the resulting a,β-dialkylcinnamonitriles." Tetrahedron Lett. 1972, 13(11), 1003-6.*
Seux, R. et al. "Decyanation of trisubstituted succinonitriles. Z and E configurations of the resulting a,β-dialkylcinnamonitriles." Tetrahedron Lett. 1972, 13(11), 1003-6. (English Translation) Translated by Phoenix Translations. Obtained from the Science and Technology Information Center (STIC), USPTO, Washington DC, Nov. 2014.*
Int'l Search Report and Written Opinion issued Sep. 5, 2014 in Int'l Application No. PCT/US2014/039290.

* cited by examiner

*Primary Examiner* — Joseph Kosack
*Assistant Examiner* — Amanda L Aguirre
(74) *Attorney, Agent, or Firm* — Panitch Schwarze Belisario & Nadel LLP

(57) ABSTRACT

Compounds and methods for preparing substituted 3-(1-amino-2-methylpentane-3-yl)phenyl compounds from an isomerically pure starting material are described. In particular, methods of preparing a 3-(1-(dimethylamino)-2-methylpentane-3-yl)phenol as a substantially optically pure (R,R) stereoisomer are described. Using a method of the present invention, only the (R,R) and (S,S) stereoisomers of the target compound are produced, increasing the yield and stereoselectivity of the desired (R,R) stereoisomer.

17 Claims, No Drawings

COMPOUNDS AND METHODS FOR PREPARING SUBSTITUTED 3-(1-AMINO-2-METHYLPENTANE-3-YL)PHENYL COMPOUNDS

FIELD OF THE INVENTION

Embodiments of the present invention relate to compounds and methods for preparing substituted 3-(1-amino-2-methylpentane-3-yl)phenyl compounds with improved stereoselectivity and increased yield of the desired stereoisomers and method for preparing the compounds. In particular, the present invention relates compounds and methods for preparing a substantially optically pure (R,R) stereoisomer of 3-(1-(dimethylamino)-2-methylpentane-3-yl)phenol (tapentadol) from a substantially isomerically pure starting material.

BACKGROUND OF THE INVENTION

Substituted 3-(1-amino-2-methylpentane-3-yl)phenyl compounds have potent analgesic effects. One 3-(1-amino-2-methylpentane-3-yl)phenyl compound in particular that is a potent analgesic, is well tolerated, and has been FDA approved for the treatment of moderate to severe acute pain is (2R,3R)-3-(1-(dimethylamino)-2-methylpentane-3-yl)phenol, commonly known as tapentadol. Tapentadol functions via a dual mode of action as a μ-opioid receptor agonist and as a norepinephrine reuptake inhibitor. Several methods for synthesizing 3-(1-amino-2-methylpentane-3-yl)phenyl compounds via multi-step synthetic strategies have been reported in, for example, US 2002/0010178, U.S. Pat. No. 6,248,737, US 2006/0167318, WO 2011/080736, WO 2011/067714, WO 2012/001571, and WO 2012/103799. Additional strategies for synthesizing 3-(1-amino-2-methylpentane-3-yl)phenyl compounds were recently described by Buschmann et al. in U.S. Patent Application Publication No. 2011/0306793.

However, all of the conventional strategies for producing 3-(1-(dimethylamino)-2-methylpentane-3-yl) phenol compounds do not use enantiomerically or isomerically pure starting materials and in the absence of using complex, expensive stereoselective or chiral reagents, yield a mixture of all four possible diastereomers of the resulting 3-(1-dimethylamino)-2-methylpentane-3-yl)phenol compound. This results in the production of undesired stereoisomers upon reduction, which ultimately decreases the yield of the desired stereoisomer. The production of a mixture of all four diastereomers also necessitates complex purification techniques and separation of the mixture in order to obtain the desired stereoisomer in its optically pure form, further decreasing product yield.

Thus, a need exists for an efficient, high yielding synthetic method for obtaining 3-(1-(dimethylamino)-2-methylpentane-3-yl)phenol compounds with improved stereoselectivity and increased yield of the desired stereoisomers. Preferably, the method allows for the synthesis of the desired stereoisomer in increased yield by suppressing the synthesis of the undesired stereoisomers using common, inexpensive reagents.

BRIEF SUMMARY OF THE INVENTION

The present invention is directed to compounds and methods for preparing substituted 3-(1-amino-2-methylpentane-3-yl)phenyl compounds with improved stereoselectivity and increased yield using common, inexpensive reagents. In particular, the present invention provides a method for synthesizing substituted 3-(1-amino-2-methylpentane-3-yl)phenyl compounds as a mixture of (R,R) and (S,S) stereoisomers that is substantially free of the (R,S) and (S,R) stereoisomers, and more particularly, a method for preparing such compounds as a substantially optically pure (R,R) stereoisomer.

According to embodiments of the present invention, a method for synthesizing a substituted 3-(1-amino-2-methylpentane-3-yl)phenyl compound with improved stereoselectivity and increased yield utilizes a novel substantially pure E-isomer of a 3-(3-hydroxyphenyl)-2-methylpent-2-enenitrile derivative as the starting material in order to inhibit synthesis of 2 undesired stereoisomers, the (R,S) and (S,R) stereoisomers, thereby increasing the yield and ease of synthesis of the desired (R,R) stereoisomer. Thus, the present invention also relates to a substantially pure E-isomer of 3-(3-hydroxyphenyl)-2-methylpent-2-enenitrile derivatives and methods of synthesizing compounds thereof.

In one general aspect, the present invention relates to a substantially pure E-isomer of a compound according to formula (I):

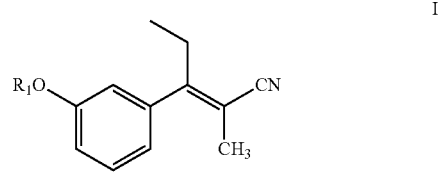

I or a pharmaceutically acceptable salt thereof, wherein $R_1$ represents a hydrogen, aliphatic, aryl, or phenolic oxygen protecting group.

In another general aspect, the present invention relates to a method of preparing a substantially pure E-isomer of a compound according to formula (I), the method comprising:
 (i) reacting a compound of formula (II):

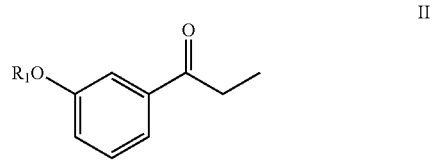

II or a pharmaceutically acceptable salt thereof, with a cyanoethyl phosphonic acid derivative of formula (III):

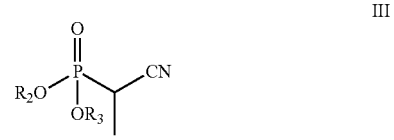

III thereby obtaining a mixture comprising the E-isomer and Z-isomer of the compound of formula (I) or the pharmaceutically acceptable salt thereof; and (ii) separating the E-isomer from the Z isomer in the mixture, thereby obtaining the substantially pure E-isomer of the compound of formula (I) or the pharmaceutically acceptable salt thereof, wherein $R_1$ represents a hydrogen, aliphatic, aryl, or phenolic oxygen protecting group, and each of $R_2$ and $R_3$ independently represents a hydrogen, alkyl, or aryl.

In a preferred embodiment, $R_1$ represents a hydrogen or methyl.

In yet another general aspect, the present invention relates to a method of preparing a compound of formula (V):

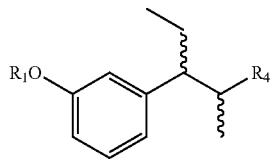

V or a pharmaceutically acceptable salt thereof, as a mixture of (R,R) and (S,S) stereoisomers that is substantially free of (R,S) and (S,R) stereoisomers, the method comprising reacting a substantially pure E-isomer of a compound of formula (I):

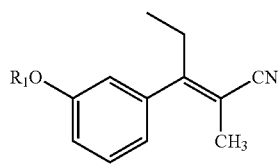

I or a pharmaceutically acceptable salt thereof with one or more reducing agents, and optionally an alkylating agent, thereby obtaining the compound of formula (V) or the pharmaceutically acceptable salt thereof as the mixture of (R,R) and (S,S) stereoisomers that is substantially free of (R,S) and (S,R) stereoisomers, wherein $R_1$ represents a hydrogen, aliphatic, aryl, or phenolic oxygen protecting group, $R_4$ represents CN or $CH_2N(R_5)_2$, and $R_5$ represents a hydrogen or alkyl.

In a preferred embodiment, the mixture of (R,R) and (S,S) stereoisomers of the compound of formula (V) is separated to obtain a substantially optically pure (R,R) stereoisomer of the compound of formula (V) or a pharmaceutically acceptable salt thereof. Preferably the mixture is separated by chromatography, more preferably by continuous chromatography, and most preferably by simulated moving bed chromatography (SMB).

Yet another general aspect of the present invention relates to a method of preparing a substantially optically pure (R,R) stereoisomer of a compound of formula (VII):

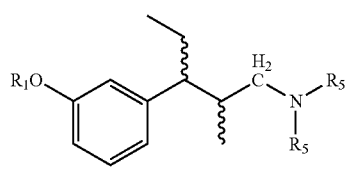

VII or a pharmaceutically acceptable salt thereof, wherein $R_1$ represents a hydrogen, aliphatic, aryl, or phenolic oxygen protecting group, and $R_5$ represents a hydrogen or alkyl.

In one embodiment, a method of preparing a substantially optically pure (R,R) stereoisomer of the compound of formula (VII) or the pharmaceutically acceptable salt thereof comprises:

(i) reducing a substantially pure E-isomer of a compound of formula (I):

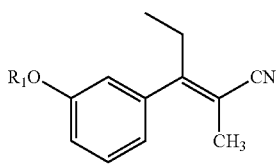

I or a pharmaceutically acceptable salt thereof, thereby obtaining a compound of formula (VI):

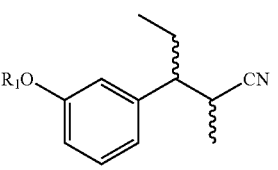

VI or a pharmaceutically acceptable salt thereof as a mixture of (R,R) and (S,S) stereoisomers that is substantially free of (R,S) and (S,R) stereoisomers, wherein $R_1$ represents a hydrogen, aliphatic, aryl, or phenolic oxygen protecting group;

(ii) separating the (R,R) and (S,S) stereoisomers in the mixture, thereby obtaining a substantially optically pure (R,R) stereoisomer of the compound of formula (VI) or the pharmaceutically acceptable salt thereof; and (iii) reacting the substantially optically pure (R,R) stereoisomer of the compound of formula (VI) or the pharmaceutically acceptable salt thereof with a reducing agent, and optionally an alkylating agent, thereby obtaining the substantially optically pure (R,R) stereoisomer of the compound of formula (VII) or the pharmaceutically acceptable salt thereof.

In another embodiment, a method of preparing a substantially optically pure (R,R) stereoisomer of the compound of formula (VII) or the pharmaceutically acceptable salt thereof comprises:

(i) reacting a substantially pure E-isomer of a compound of formula (I):

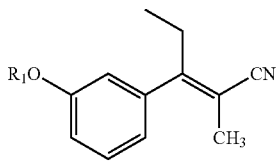

I or a pharmaceutically acceptable salt thereof with a reducing agent, and optionally an alkylating agent, thereby obtaining a compound of formula (IV):

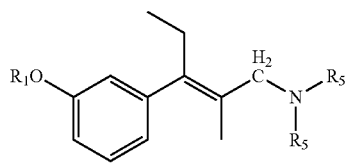

IV

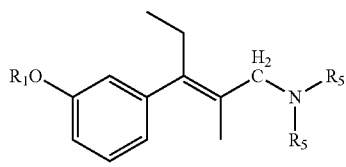

IV or a pharmaceutically acceptable salt thereof, wherein R₁ represents a hydrogen, aliphatic, aryl, or phenolic oxygen protecting group, and R₅ represents a hydrogen or alkyl;

(ii) reducing the compound of formula (IV) or the pharmaceutically acceptable salt thereof, thereby obtaining the compound of formula (VII) or the pharmaceutically acceptable salt thereof in a mixture of (R,R) and (S,S) stereoisomers that is substantially free of (R,S) and (S,R) stereoisomers; and (iii) separating the (R,R) and (S,S) stereoisomers in the mixture, thereby obtaining the substantially optically pure (R,R) stereoisomer of the compound of formula (VII) or a pharmaceutically acceptable salt thereof.

In yet another embodiment of the present invention, a method of preparing a substantially optically pure (R,R) stereoisomer of the compound of formula (VII) or the pharmaceutically acceptable salt thereof comprises:

(i) reacting a substantially pure E-isomer of a compound of formula (I):

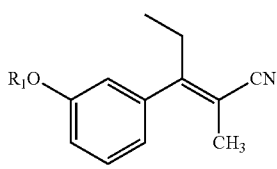

I or a pharmaceutically acceptable salt thereof with one or more reducing agents, and optionally an alkylating agent, thereby obtaining a compound of formula (VII) or a pharmaceutically acceptable salt thereof in a mixture of (R,R) and (S,S) stereoisomers that is substantially free of (R,S) and (S,R) stereoisomers, wherein R₁ represents a hydrogen, aliphatic, aryl, or phenolic oxygen protecting group; and (ii) separating the (R,R) and (S,S) stereoisomers in the mixture, thereby obtaining the substantially optically pure (R,R) stereoisomer of the compound of formula (VII) or the pharmaceutically acceptable salt thereof.

According to a preferred embodiment, a method of the present invention yields a substantially optically pure (R,R) stereoisomer of a compound of formula (VII) or a pharmaceutically acceptable salt thereof, wherein R₁ represents hydrogen and R₅ represents methyl.

In yet another preferred embodiment, the mixture of (R,R) and (S,S) stereoisomers of compound of formula (VII) is separated by chromatography, more preferably by continuous chromatography, and even more preferably by simulated moving bed chromatography (SMB).

In yet another general aspect, the present invention relates to a substantially pure E-isomer of a compound according to formula (IV):

or a pharmaceutically acceptable salt thereof, wherein R₁ represents a hydrogen, aliphatic, aryl, or phenolic oxygen protecting group and R₅ represents a hydrogen or alkyl, and methods of preparing the substantially pure E-isomer of the compound of formula (IV), or a pharmaceutically acceptable salt thereof.

According to embodiments of the present invention, a method for preparing a substantially pure E-isomer of a compound according to formula (IV) or a pharmaceutically acceptable salt thereof, comprises reacting a substantially pure E-isomer of a compound of formula (I) or a pharmaceutically acceptable salt thereof with a reducing agent and optionally an alkylating reagent in the presence of a nickel catalyst.

Other aspects, features and advantages of the invention will be apparent from the following disclosure, including the detailed description of the invention and its preferred embodiments and the appended claims.

DETAILED DESCRIPTION OF THE INVENTION

Unless defined otherwise, all technical and scientific terms used herein have the same meaning as is commonly understood by one of ordinary skill in the art to which this invention pertains. All publications and patents referred to herein are incorporated by reference. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

It must be noted that as used herein and in the appended claims, the singular forms "a," "an," and "the" include plural reference unless the context clearly dictates otherwise.

The phrase "pharmaceutically acceptable salt" as used herein means those salts of a compound of interest that are safe and effective for administration to a mammal and that possess the desired biological activity. Pharmaceutically acceptable acid addition salts include, but are not limited to hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compositions used in the present invention can form pharmaceutically acceptable salts with various amino acids. Suitable base salts include, but are not limited to, aluminum, calcium, lithium, magnesium, potassium, sodium, zinc, bismuth, and diethanolamine salts. For a review of pharmaceutically acceptable salts see Berge et al., *J. Pharm. Sci.* (1977) 66, 1-19, incorporated herein by reference.

Preferably, a pharmaceutically acceptable salt of a compound produced by a method of the present invention is an acid addition salt, and more preferably a hydrochloride salt. In view of the present disclosure, a hydrochloride salt can be produced, for example, by reacting a compound produced by a method of the present invention with HCl in an organic solvent, such as dioxane. Methods for preparing other salts in addition to the hydrochloride salt will be well known to one of ordinary skill in the art.

As used herein, the term "aliphatic" or "aliphatic group" refers to a saturated or unsaturated linear (i.e. straight chain) or branched hydrocarbon group, and non-aromatic rings (i.e. alicyclic). Aliphatics can be saturated, meaning that the carbon atoms are joined together by single bonds (alkanes), or unsaturated, meaning that the carbon atoms are joined together by double bonds (alkenes) or triple bonds (alkynes). Aliphatic groups encompass alkyl, alkenyl, alkynl, and alicyclic groups.

Unless otherwise noted, the term "alkyl" as used herein means a saturated, unbranched or branched hydrocarbon chain containing at least one carbon atom. An alkyl group can be unsubstituted or substituted with one or more suitable substituents. Examples of unbranched alkyls include, but are not limited to, methyl, ethyl, propyl, butyl, pentyl, hexyl, heptyl, octyl, nonyl, and decyl. Examples of branched alkyls include, but are not limited to isopropyl, isobutyl, 2-methylpentyl, 3-methylpentyl, 2,2-dimethylbutyl, 2,3-dimethylbutyl, 2-methylhexyl, 2,3-dimethylhexyl, 2,2-dimethylhexyl, and 3,3-dimethylhexyl.

As used herein, the term "alkenyl" means an unsaturated, branched or unbranched hydrocarbon chain having one or more carbon-carbon double bonds. An alkenyl group can be unsubstituted or substituted with one or more suitable substituents. Examples of unbranched alkenyls include, but are not limited to, ethenyl, propenyl, butenyl, pentenyl, hexenyl, heptenyl, octynyl, nonenyl, and decenyl. Examples of branched alkenyls include, but are not limited to isobutenyl, 2-methyl-2-pentenyl, 3-methyl-2-pentenyl, 2,2-dimethyl-2-butenyl, and 2-methyl-3-hexenyl.

As used herein, the term "alkynl" means an unsaturated, branched or unbranched hydrocarbon chain having one or more carbon-carbon triple bonds. An alkynl group can be unsubstituted or substituted with one or more suitable substituents. Examples of unbranched alkenyls include, but are not limited to ethynyl, propynyl, butynyl, pentynyl, hexynyl, heptynyl, octynyl, nonynyl, and decynyl. Examples of branched alkynyls include, but are not limited to, 3-methyl-1-butynl, 3,3-dimethyl-1-butynl, and 3-methyl-1-pentynl.

Unless otherwise noted, the term "alicyclic" refers to an aliphatic, cyclic hydrocarbon having at least three carbon atoms. An alicyclic group can be saturated (cycloalkane), or unsaturated, meaning that at least two carbon atoms are joined together by a double bond (cycloalkene) or triple bond (cycloalkyne). An alicyclic group can be unsubstituted or substituted with one or more suitable substituents. Unless otherwise noted, "cycloalkyl" refers to a saturated, unbranched or branched cyclic hydrocarbon; "cycloalkenyl" refers to an unsaturated, unbranched or branched cyclic hydrocarbon having one or more carbon-carbon double bonds; and "cycloalkynyl" refers to an unsaturated, unbranched or branched cyclic hydrocarbon having one or more carbon-carbon triple bonds. Non-limiting examples of cycloalkyl groups include cyclopenytl, cyclohexyl, cyclooctyl, 1-methylcyclohexyl, and 1,2-dimethylcyclopentyl; non-limiting examples of cycloalkenyl groups include cyclopentenyl, cyclohexenyl, and 1-methyl-1-cyclohexenyl; and non-limiting examples of cycloalkynl groups include cyclooctnyl and 3-methyl-1-cyclooctynyl.

As used herein, the term "aryl" is intended to mean any substituent derived from an aromatic ring. An aryl substituent can be a single aromatic ring, or multiple aromatic rings. The term "aryl" also encompasses "heteroaryl." A "heteroaryl" group as defined herein means an aryl group, wherein one or more carbons of an aromatic ring is substituted with a heteroatom, such as oxygen, nitrogen, or sulfur. Examples of aryl groups include, but are not limited to, phenyl, napthyl, methylbenzyl, and dimethylbenzyl. Examples of heteroaryl groups include, but are not limited to, pyridyl, furanyl and thienyl. Aryl and heteroaryl groups can be substituted with one or more suitable substituents.

Unless otherwise noted, the term "alkoxy" as used herein, denotes a unit having the general formula —OR wherein R is an aliphatic (i.e. alkyl, alkenyl, alkynyl, alicyclic) or aryl unit. An alkoxy group can be, for example, methoxy, ethenyloxy, and ethynyloxy. Other examples of alkoxy groups include, but are not limited to, ethoxy, n-propoxy, butoxy, isobutoxy, sec-butoxy, t-butoxy, n-hexyloxy, phenoxy and the like. When a particular group is "substituted" (i.e. aliphatic, alicyclic, alkyl, alkenyl, alkynl, aryl, or heteroaryl), that group can have one or more substituents preferably from one to five substituents, more preferably from one to three substituents, most preferably from one to two substituents, independently selected from the list of substituents.

Representative examples of suitable substituents for which a particular group (ie. aliphatic, alicyclic, alkyl, alkenyl, alkynl, aryl, or heteroaryl) can be substituted with include, but are not limited to, halogens, such as fluoro, chloro, bromo, and iodo; hydroxyl; alkoxy, such as methoxy, ethoxy, and propoxy; alkyl, such as methyl, ethyl and propyl; nitriles, such as cyano; and nitro.

As used herein, the term "phenolic oxygen protecting group" refers to a substituent attached to a phenolic oxygen that renders the phenolic oxygen inert, or non-reactive, until the substituent is removed. The substituent essentially "protects" the phenolic oxygen from undesired side reactions, transformations, or degradation, and therefore can also be referred to as a "protecting group." Non-limiting examples of suitable phenolic oxygen protecting groups include silyl-based protecting groups, such as tert-butyl dimethylsilyl (TBDMS), trimethylsilyl (TMS), triethylsilyl, methyldiethylsilyl, dimethylethylsilyl, tert-butyldiphenylsilyl (TBDPS), triisopropylsilyl (TIPS), phenyldimethylsilyl, and triphenylsilyl; ester groups, such acetyl; and carbonates, such as tert-butylcarbonate. One skilled in the art will be able to readily determine appropriate reaction conditions for introduction a phenolic oxygen protecting group onto a compound of the present invention, as well as the appropriate reaction conditions for removing the phenolic oxygen protecting group. For a review of protecting groups and in particular phenolic oxygen protecting groups, see Wuts, P.G.M. and Green, T. W. *Green's Protective Groups in Organic Synthesis*, 4th Edition (2006), incorporated herein by reference. Preferred phenolic oxygen protecting groups for use in the present invention include TBDMS.

As used herein, the term "stereoisomers" refers to at least two compounds having the same molecular formula and connectivity of atoms, but having a different arrangement of atoms in a three-dimensional space. A stereoisomer often, but not exclusively has a chiral carbon atom. As used herein, a "chiral carbon atom" is a carbon atom in which four different atoms or four different groups of atoms are attached. Compounds containing chiral carbon atoms typically, but no always, rotate the plane of polarized light, and are thus referred to as being "optically active." For example, a compound of formula (V) according to the invention has two chiral carbon atoms, indicated by asterisks:

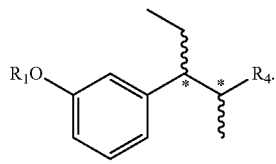

Each of these chiral carbon atoms is attached to four different groups of atoms.

A stereoisomer can be, for example, an enantiomer or a diastereomer. As used herein, the term "enantiomers" refers to a pair of compounds which are non-superimposable mirror images of one another. In other words, an "enantiomer" is a stereoisomer that cannot be superimposed on its mirror image. As used herein, "diasteromers" are stereoisomers which are not mirror images. Diastereomers and enantiomers have at least one chiral carbon atom, and can be referred to as optical isomers.

The "RS" convention for designating the three dimensional arrangement of atoms at a chiral carbon atom will be employed herein in the naming of stereoisomers. The designation of "S" or "R" for a given chiral carbon atom is based upon "priority rules" well known to those skilled in the art.

According to embodiments of the present invention, compounds of formulas (V), (VI), and (VII) have four possible stereoisomers, which are enantiomers or diastereomers, designated as (R,R), (S,S), (R,S) and (S,R). For example, compounds of formulas (V), (VI), and (VII) of the present invention have two pairs of enantiomers, a pair of (R,R) and (S,S) enantiomers, and a pair of (R,S) and (S,R) enantiomers. In addition, (R,R) and (R,S) stereoisomers of formulas (V), (VI), and (VII) are diastereomers; (R,R) and (S,R) are diastereomers; (S,S) and (S,R) are diastereomers; and (S,S) and (R,S) are also diastereomers. Significantly, a method of the present invention for preparing a compound of formula (V), (VI), or (VI) produces only the (R,R) and (S,S) stereoisomers, and not the (R,S) or (S,R) stereoisomers.

Unless defined otherwise, a "mixture of stereoisomers" or "stereoisomeric mixture" refers to a mixture or composition containing at least two stereoisomers of a particular compound. A mixture of stereoisomers can be, for example, a mixture of (R,R) and (S,S) stereoisomers, a mixture of (R,R), (S,S), (R,S) and (S,R) stereoisomers, or a mixture (R,S) and (S,R) stereoisomers. According to embodiments of the present invention, a mixture of stereoisomers is a mixture of (R,R) and (S,S) stereoisomers that is substantially free of the (R,S) and (S,R) stereoisomers.

By "substantially free of the (R,S) and (S,R) stereoisomers," it is meant that the mixture is largely but not wholly free of the (R,S) and (S,R) stereoisomers. According to embodiments of the present invention, a mixture "substantially free of the (R,S) and (S,R) stereoisomers" contains 5% (w/w) or less of the (R,S) and (S,R) stereoisomers in total, such as, for example, 5%, 4.5%, 4%, 3.5%, 3%, 2.5%, 2%, 1.5%, 1%, 0.5%, or 0% (w/w). In other words, according to embodiments of the present invention, a mixture of (R,R) and (S,S) stereoisomers that is substantially free of the (R,S) and (S,R) stereoisomers contains 95% or greater of the (R,R) and (S,S) stereoisomers in total, such as, for example, 95%, 95.5%, 96%, 96.5%, 97%, 97.5%, 98%, 98.5%, 99%, 99.5%, or 100% (w/w).

Preferably, a mixture of (R,R) and (S,S) stereoisomers according to the invention is an equal mixture of (R,R) and (S,S) stereoisomers, i.e., 50% (R,R) and 50% (S,S). However, a mixture of stereoisomers of (R,R): (S,S) can also be, for example, 10%:90%, 20%:80%, 30%:70%, 40%:60%, 45%: 55%, 55%:45%, 60%:40%, 70%: 30%, 80%:20%, or 90%, 10%.

In a compound according to formula (V):

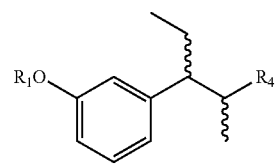

or a pharmaceutically acceptable salt thereof prepared by a method of the present invention, $R_1$ represents a hydrogen, aliphatic, aryl, or phenolic oxygen protecting group, $R_4$ represents CN or $CH_2N(R_5)_2$, and $R_5$ represents a hydrogen or alkyl. According to embodiments of the present invention, the compound of formula (V) is synthesized as a mixture of (R,R) and (S,S) stereoisomers that is substantially free of the (S,R) and (R,S) stereoisomers. In a preferred embodiment, the mixture of (R,R) and (S,S) stereoisomers is separated, thereby obtaining a substantially optically pure (R,R) stereoisomer.

In a preferred embodiment of the present invention, the compound according to formula (V) is a compound according to formula (VII):

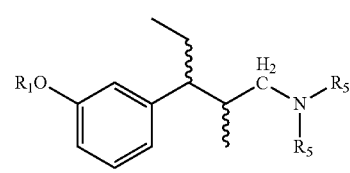

or a pharmaceutically acceptable salt thereof, wherein $R_1$ represents a hydrogen, aliphatic, aryl, or phenolic oxygen protecting group, and $R_5$ represents a hydrogen or alkyl. Preferably, $R_1$ is a hydrogen or aliphatic group, in particular an alkyl group such as methyl. In a particularly preferred embodiment, $R_1$ represents a hydrogen and $R_5$ represents a methyl.

In a most preferred embodiment, the compound of formula (VII), or a pharmaceutically acceptable salt thereof, obtained by a method of the present invention is commonly known as tapentadol. As used herein, "tapentadol," or (2R,3R)-3-(1-dimethylamino)-2-methylpentane-3-yl)phenol is a substantially optically pure (R,R) stereoisomer of a compound of formula (VII), or a pharmaceutically acceptable salt thereof, wherein $R_1$ represents hydrogen and $R_5$ represents methyl. An (R,R) stereoisomer of a compound of formula (VII) has the following chemical structure:

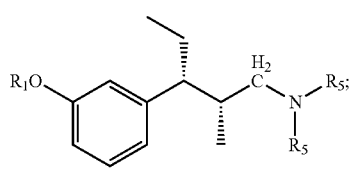

and tapentadol has the following chemical structure:

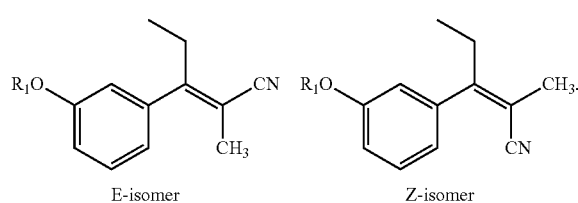

As used herein, the term "substantially optically pure" when used with reference to a stereoisomer, diastereomer, or enantiomer of a compound means substantially or largely, but not wholly, free of the other stereoisomers, diastereomers, or enantiomer of the compound, but not necessarily from other materials. According to embodiments of the present invention, a "substantially optically pure" stereoisomer, diastereomer, or enantiomer of a compound comprises 95% (by weight, w/w) or greater, such as 95%, 95.5%, 96%, 96.5%, 97%, 97.5%, 98%, 98.5%, 99%, 99.5%, or 100% (w/w) of the stereoisomer, diastereomer, or enantiomer relative to the total weight of the stereoisomers, diastereomers, or enantiomers of the compound. As an illustrative example, a substantially optically pure (R,R) stereoisomer of a compound synthesized according a method of the present invention can comprise 95% (w/w) or more of the (R,R) stereoisomer relative to the total optical isomers of the compound. Different purity levels may be required for different "substantially optically pure" compounds.

As used herein, the terms "E-isomer" and "Z-isomer" refer to compounds having at least one substituted carbon-carbon double bond with the same chemical formula and connectivity of atoms, but having a different geometric configuration, i.e. arrangement of substituents about a carbon-carbon double bond. The naming convention of "E" and "Z" for designating the particular geometric configuration about a carbon-carbon double bond is based upon "priority rules" well known to one skilled in the art. For example, a compound of formula (I) of the present invention can be an E-isomer or a Z-isomer:

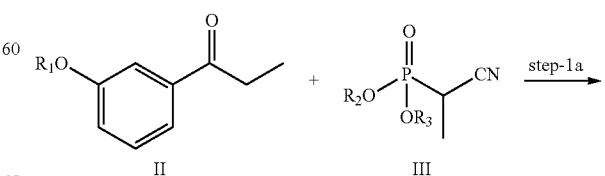

E-isomer               Z-isomer

Preferably, a compound of formula (I) is an E-isomer.

In the present invention, it has been found that a compound of formula (V), and preferably a compound of formula (VII), can be synthesized with improved yield and stereoselectivity by utilizing a novel isomerically pure starting material. In particular, the isomerically pure starting material used in a method of the present invention is a substantially pure E-isomer of a compound of formula (I):

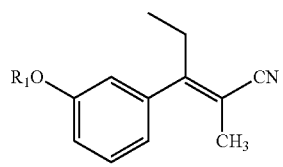

or a pharmaceutically acceptable salt thereof, wherein $R_1$ represents a hydrogen, aliphatic, aryl, or phenolic oxygen protecting group.

As used herein, the term "substantially pure" when referring to an E-isomer of a compound that can exist in the E and Z isomeric forms (i.e. a compound with a substituted carbon-carbon bond) means substantially, i.e., largely but not wholly, free of the Z isomer of the compound, but not necessarily free of other materials. According to embodiments of the present invention, a "substantially pure" E isomer of a compound of formula (I) has a ratio of E-isomer/total Z-isomer and E-isomer of the compound that is 95% (w/w) or greater, such as 95%, 95.5%, 96%, 96.5%, 97%, 97.5%, 98%, 98.5%, 99%, 99.5%, or 100% (w/w).

Because only the E-isomer is used in a method of the present invention, reduction of the alkene moiety of a compound of formula (I) to obtain a compound of formula (V), and preferably a compound of formula (VII), results in production of only the (R,R) and (S,S) stereoisomers. Thus, the preferred (R,R) stereoisomer is produced with greater stereoselectivity and in increased yield, as compared to a reduction reaction performed on a mixture of both the E and Z isomers of a compound of formula (I). According to embodiments of the present invention, using substantially pure (E) isomer as a starting material provides more control over purity of the product and overcomes the low yielding and difficult resolution steps in the conventional methods Until now, compounds of formula (I) have only been produced as a mixture of E and Z isomers. Thus, in one aspect, the present invention relates to a substantially pure E-isomer of a compound of formula (I) or a pharmaceutically acceptable salt thereof, and methods of preparing a substantially pure E-isomer of a compound of formula (I). In a preferred embodiment, the substantially pure E-isomer has an E-isomer/total Z-isomer and E-isomer ratio of 95% (w/w) or greater.

In general, a compound of formula (I) is synthesized according to Scheme 1:

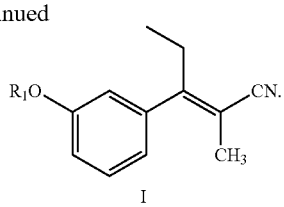

I

A compound of formula (II), or a pharmaceutically acceptable salt thereof, is reacted with a cyanoethylphosphonic acid derivative of formula (III) (step-1a), thereby obtaining a mixture comprising the E-isomer and Z-isomer of the compound of formula (I), or a pharmaceutically acceptable salt thereof, wherein $R_1$ represents a hydrogen, aliphatic, aryl, or phenolic oxygen protecting group, and each of $R_2$ and $R_3$ independently represent a hydrogen, alkyl, or aryl. Preferably, $R_1$ is a hydrogen, aliphatic (particularly alkyl), or phenolic oxygen protecting group (particularly TBDMS). In a preferred embodiment, $R_1$ is a hydrogen or methyl.

The cyanoethylphosphonic acid derivative of formula (III) is preferably diethyl 1-cyanoethylphosphonate, wherein $R_2$ and $R_3$ both represent an ethyl substituent. Cyanoethylphosphonic acid derivatives for use in a method of the present invention can be prepared according to conventional methods known to one of ordinary skill in the art, or can be obtained from commercial sources.

Preferably, step-1a according to a method of the invention is a Wittig-Horner reaction. A Wittig-Horner reaction generally refers to the conversion of an aldehyde or ketone to an alkene moiety by reacting with a phosphonate reagent under conditions that promote the conversion. Step-1a is carried out in a liquid reaction solvent in the presence of a base, and is preferably performed under inert conditions, such as under a nitrogen atmosphere. The reaction solvent is preferably an organic solvent. Examples of organic solvents for use in step-1a include tetrahydrofuran (THF), toluene, dimethylacetamide (DMAc), or other suitable solvents. Preferably the organic solvent is tetrahydrofuran. Representative examples of bases that can be used in step-1a include metal hydrides, such as sodium hydride, lithium hydride, and potassium hydride; alkoxides, such as methoxide, ethoxide, and tert-butoxide, and preferably sodium or potassium alkoxides; and organolithium bases, such as n-butyl lithium or other suitable bases. Preferably the base is sodium hydride or potassium tert-butoxide.

The reaction parameters of step-1a, such as, for example, temperature and reaction time, can vary over a wide range depending on the particular base, solvent, and cyanoethylphosphonic acid derivative used, and the optimal value of such parameters can readily be determined by one of ordinary skill in the art. Preferably, the reaction temperature ranges from about 0° C. to about 70° C. The temperature need not remain constant over the course of the reaction but can be adjusted, for example, from 0° C. at the start of the reaction as the reagents are mixed together, to about 65° C. to allow for the reaction mixture to reflux.

The reaction of compounds II and III in step-1a can be monitored throughout the course of the reaction by removing a sample from the reaction mixture. Conventional methods for determining the progress of the reaction can be used, such as, for example, thin layer chromatography (TLC). The mixture of E and Z isomers of the compound of formula (I) obtained in step-1a can be isolated and purified from the reaction mixture by conventional methods known to skilled persons in the art, such as, for example, extraction with an organic solvent.

The mixture comprising the E and Z isomers of a compound of formula (I) obtained in step-1a is then separated, thereby obtaining a substantially pure E-isomer of a compound of formula (I). Any suitable method for obtaining resolution between the E and Z isomers of a compound of formula (I) can be used in view of the present disclosure. Preferably, the isomers are separated by chromatography, such as, for example, flash column chromatography and more particularly silica gel flash chromatography. The chromatography can be carried out using a mobile phase comprised of one or more solvents including organic solvents, ethyl acetate, alcohols, aliphatic solvents such as hexanes and heptanes, or other suitable solvents for obtaining resolution between the two isomers. Preferably, a mixture of ethyl acetate and hexanes is used as the mobile phase.

According to embodiments of the present invention, when a mixture of E and Z isomers of a compound of formula (I) is separated to obtain a substantially pure E-isomer, the substantially pure Z-isomer is also obtained. Thus, in a preferred embodiment, the substantially pure Z-isomer is reacted with a base in an isomerization reaction to convert the Z-isomer into the desired E-isomer. In this way, the undesirable Z-isomer is recycled back to the desirable E-isomer, which can then subsequently be used in a method of the present invention for synthesizing a compound of formula (V), and preferably a compound of formula (VII).

A method according to the present invention for isomerizing the Z-isomer to the E-isomer of a compound of formula (I), or a pharmaceutically acceptable salt thereof, comprises reacting the Z-isomer with a base to obtain a second mixture comprising the E-isomer and Z-isomer of the compound of formula (I), or the pharmaceutically acceptable salt thereof. This second mixture of E and Z isomers is then separated, preferably by chromatography as discussed above, to thereby obtain the substantially pure E-isomer. The substantially pure Z-isomer obtained from separation of the second mixture of isomers can again be subjected to an isomerization reaction. The number of times the isomerization reaction can be performed is not limited in any way.

Any suitable base can be used in the isomerization reaction in view of the present disclosure, including, but not limited to, alkoxides such as methoxide, ethoxide, isopropoxide, and tert-butoxide, preferably potassium alkoxides, or other suitable base. In a preferred embodiment, the base is an alkoxide, and in a more preferred embodiment, the base is potassium tert-butoxide. The isomerization reaction is preferably carried out in a liquid reaction solvent, and preferably an organic solvent. Representative examples of organic solvents that can be used include tetrahydrofuran (THF), toluene, and dimethylacetamide (DMAc). Preferably the organic solvent is tetrahydrofuran. Reaction time and temperature can be appropriately adjusted to optimize the equilibrium of the isomerization. The reaction is complete when equilibrium is reached. One skilled in the art will readily be able to determine when equilibrium has been achieved using standard techniques, such as, for example, thin layer chromatography (TLC).

In a particular embodiment, a compound of formula (I) or a pharmaceutically acceptable salt thereof, wherein $R_1$ is not hydrogen (ie. an aliphatic, alkyl, aryl, or phenolic oxygen protecting group) can be deprotected. Either a substantially pure isomer, or a mixture of the two isomers can be subjected to a deprotection reaction. The deprotected compound of formula (I) can be used in a method according to the present invention for preparing a compound of formula (V), and preferably a compound of formula (VII). The deprotection conditions will depend on the nature of the $R_1$ group, and one of ordinary skill in the art will be readily able to determine the deprotection reaction conditions. For example, a compound of formula (I) wherein R1 represents a methyl can be reacted with boron tribromide in an organic solvent such as dichloromethane to obtain a compound of formula (I) wherein $R_1$ represents a hydrogen.

Another aspect of the present invention relates to a method of preparing a compound of formula (V):

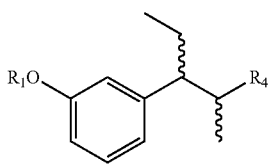

V or a pharmaceutically acceptable salt thereof, wherein $R_1$ represents hydrogen, aliphatic, aryl, or a phenolic oxygen protecting group, $R_4$ represents CN or $CH_2N(R_5)_2$, and $R_5$ represents a hydrogen or alkyl. According to embodiments of the present invention, the method utilizes a substantially pure E-isomer of a compound of formula (I) as the starting material. A compound of formula (V), or a pharmaceutically acceptable salt thereof is prepared as a mixture of (R,R) and (S,S) stereoisomers, and preferably as a substantially optically pure (R,R) stereoisomer.

In one embodiment, a method for preparing a compound of formula (V), or a pharmaceutically acceptable salt thereof, as a mixture of (R,R) and (S,S) stereoisomers that is substantially free of the (R,S) and (S,R) stereoisomers according to the present invention comprises reacting a substantially pure E-isomer of a compound of formula (I) with one or more reducing agents in the reduction step-2a as shown below in Scheme 2:

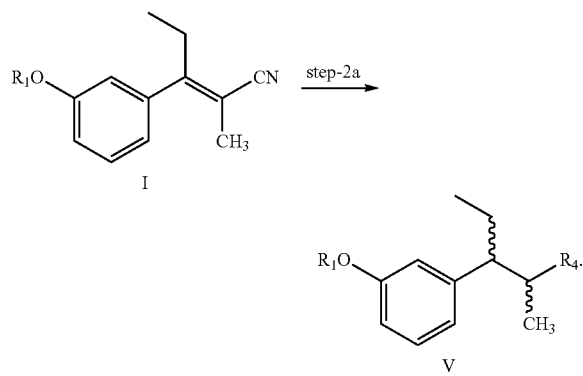

As used herein, the term "reducing agent" encompasses any reagent that catalyzes a reduction reaction. In particular, the term "reducing agent" refers to any reagent that can be used to reduce an alkene to an alkane, a cyano group to an amine, or can be used to perform both types of reduction reactions. Reduction reactions can occur via homogeneous catalysis or via heterogeneous catalysis.

As used herein, the term "homogeneous catalysis" refers to a reduction reaction wherein the reducing agent is present in the same phase (i.e. solid, liquid, gas) as the reactants. As used herein, the term "heterogeneous catalysis" refers to a reduction reaction wherein the reducing agent is present in a different phase from the reactants.

A reduction reaction that occurs via homogeneous catalysis according to a method of the present invention can be catalyzed by a reducing agent that is a transition metal complex of rhodium, iridium or ruthenium. Preferably, the reducing agent for reduction via homogeneous catalysis is co-dissolved in the reaction solvent with the reactants.

A reduction reaction that occurs via heterogeneous catalysis according to a method of the present invention can be catalyzed by a reducing agent that is present as a solid in a liquid reaction solvent in which the reactants are dissolved. In this case, the reducing agent can comprise one or more transition metals. Non-limiting examples of suitable transition metals include copper, silver, gold, zinc, cadmium, mercury, vanadium, niobium, tantalum, chromium, molybdenum, tungsten, ruthenium, osmium, cobalt, rhodium, iridium, nickel, palladium, and platinum. Preferably, the transition metal is ruthenium, rhodium, palladium, platinum, or nickel, and most preferably palladium, platinum, or nickel. One or more of the above-mentioned transition metals can be used in a reduction reaction according to the invention, and the transition metals can be present in the same or different oxidation states.

When the reduction reaction occurs via heterogeneous catalysis, one or more the above-mentioned transition metals can be deposited on an inert carrier substance, such as carbon. Thus, in a preferred embodiment of the present invention, the reducing agent is palladium on carbon, platinum on carbon, Raney nickel, or any combination thereof.

Methods for preparing reducing agents for reduction via homogeneous or heterogeneous catalysis are well known to one of ordinary skill in the art and can be prepared by any method known in view of the present disclosure.

For reduction step-2a any reducing agent in view of the present disclosure can be used to catalyze the reaction. The E-isomer of a compound of formula (I) is preferably mixed with or dissolved in a liquid reaction solvent, such that under the particular reaction conditions used, the reduction step-2a is carried out in the liquid phase. Solvents that can be used for the reduction step-2a include, but are not limited to, methanol, ethanol, propanol, isopropanol, butanol, n-pentane, n-hexane, n-heptane, toluene, ethyl acetate, and mixtures thereof, or any other suitable solvent. Preferably, the solvent is methanol or isopropanol. Step-2a is also carried out in the presence of hydrogen. Preferably, the hydrogen used is in gaseous form. The hydrogen gas can be at least in part dissolved in the liquid reaction solvent.

The reaction parameters for the reduction step-2a, such as pressure, temperature, or reaction time can vary over a wide range. Preferably, the temperature during the reduction step-2a ranges from about 0 to 250° C., more preferably from 15 to 180° C., and most preferably from 15 to 30° C. The reduction can be carried out at reduced pressure, normal pressure, or elevated pressure. Preferably, the reaction is carried out under a pressure ranging from 1-100 psi and is most preferably carried out at a pressure of about 50 psi, however a pressure above 100 psi can be used as well. The reaction time will vary depending on the particular catalyst, temperature, and pressure, as well as other variables regarding the reaction conditions.

The total amount of reducing agent used in the reduction step-2a can also vary over a wide range and will depend upon various factors such as the particular reducing agent, the reaction parameters, and the amount of the starting material (i.e. E-isomer of a compound of formula (I)) present in the reaction mixture).

In a preferred embodiment, the reduction step-2a is carried out via heterogeneous catalysis. Any suitable catalyst for performing heterogenous catalysis can be used. Preferably, the reducing agent is selected from the group consisting of palladium on carbon, platinum on carbon, and nickel catalysts, particularly Raney nickel or Sponge nickel.

Step-2a can also optionally be performed in the presence of an alkylating agent. As used herein, the term "alkylating agent" is intended to refer to a reagent capable of substituting a hydrogen for an alkyl group. An alkylating agent for use in the present invention is preferably a reagent capable of alkylating an amine group. Any suitable alkylating agent for alkylating an amine can be used, such as formaldehyde/methanol. Preferably, when the optional alkylation is desired, reduction step-2a is performed in the presence of formaldehyde/methanol.

In a preferred embodiment, the mixture of (R,R) and (S,S) stereoisomers obtained from reduction step-2a is separated to obtain a substantially optically pure (R,R) stereoisomer of a compound of formula (V). The separation can be carried out by methods known in the art in view of the present invention, such as chromatography or recrystallization, preferably by chromatography. Any chromatographic separation technique for resolving the two stereoisomers can be used including, but not limited to, batch chromatography, supercritical fluid chromatography, and continuous chromatography.

In one embodiment, the chromatography comprises batch chromatography either under low pressure, moderate pressure (i.e. flash chromatography), or high pressure (i.e. preparatory high performance liquid chromatography). In another embodiment, the chromatography comprises supercritical fluid chromatography. In yet another embodiment, the chromatography comprises continuous chromatography. Non-limiting examples of continuous chromatography include simulated moving bed chromatography (SMB) and a Varicol process.

In a preferred embodiment, the chromatography comprises one or more selected from the group consisting of batch chromatography, supercritical fluid chromatography, and continuous chromatography. In a more preferred embodiment, the chromatography comprises a Varicol process. In a most preferred embodiment, the chromatography comprises SMB. Embodiments of the present invention also include chromatography comprising variations of SMB and a Varicol process.

According to embodiments of the present invention, the separation can be performed using a chromatographic media that allows for the resolution of the two stereoisomers (i.e. (R,R) and (S,S)). In one embodiment, the chromatographic media is a silica based media. In another embodiment, the chromatographic media is a silica based media that has a mono-distributed particle size with an average particle size distribution comprised between about 3 and 50 micrometers. In yet another embodiment, the chromatographic media comprises a polymer that exhibits preferential selectivity towards one of the stereoisomers. The chromatographic media can be coated with the polymer, or bound to the polymer, such as, for example, via a covalent bond. Thus, in yet another embodiment, the chromatographic media is coated with an amylose or cellulose based chiral selector. Even further, in another embodiment, the amylose or cellulose based chiral selector is permanently bonded to the chromatographic media. For example, the chromatographic media can be a silica based media with an amylose or cellulose based chiral selector bonded to the silica based media.

In one embodiment, the chromatographic media is Chiralcel OJ manufactured by Daicel (Japan). In another embodiment, the chromatographic media is Chiralpak AD manufactured by Daicel (Japan). In yet another embodiment, the chromatographic media is Chiralpak IA manufactured by Daicel (Japan).

According to embodiments of the present invention, the chromatographic separation can be performed using a mobile phase. In one embodiment, the mobile phase comprises a single solvent or a mixture of solvents. Any solvent suitable for performing chromatography to obtain resolution between the two stereoisomers can be used in the view of the present disclosure, and preferably the mobile phase comprises a single organic solvent or a mixture of organic solvents. The solvent of the mobile phase is preferably selected from the group consisting of acetonitrile, acetone, methanol, ethanol, isopropanol, n-propanol, n-butanol, tert-butanol, hexanes, heptanes, cyclopentanes, cyclohexanes, methylcycloheptanes;, ethylacetate, methyl-tert-butyl ether, toluene, dichloromethane, trichloromethane, dichloroethane, carbon dioxide, water, and mixtures thereof. In a preferred embodiment, the mobile phase is a mixture of n-heptane and isopropanol. In a more preferred embodiment, the mobile phase is comprised of n-heptane or a mixture of n-heptane and isopropanol, wherein n-heptane is 80-100% by volume, and most preferably 90-100% by volume.

In another aspect of the present invention, a compound of formula (VII), or a pharmaceutically acceptable salt thereof, can be prepared as a mixture of (R,R) and (S,S) stereoisomers that is substantially free of the (S,R) and (R,S) stereoisomers by reducing a substantially pure E-isomer of a compound of formula (I). The reaction can be carried out in a single reduction step (step-3a), or in two separate reduction steps (step-3b followed by step-3c; or step-3d followed by step-3e) as shown below in Scheme 3:

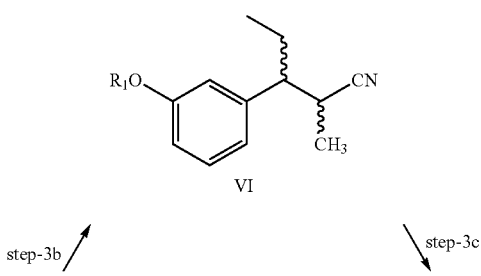

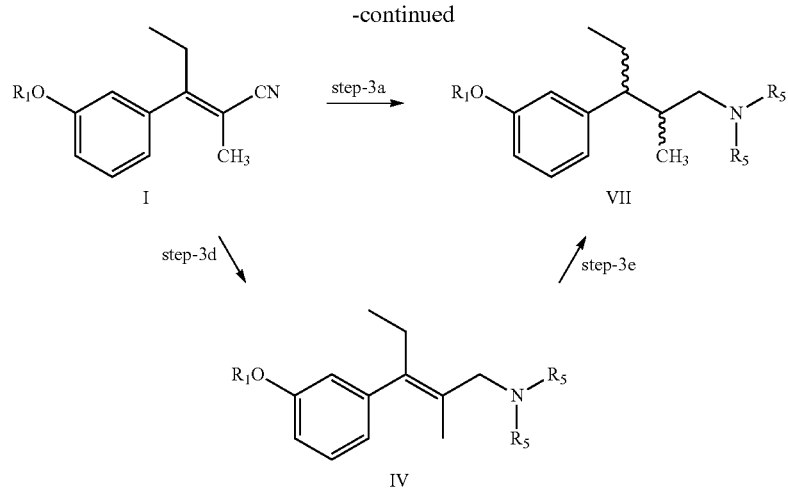

According to embodiments of the present invention, when a compound of formula (VII) is obtained from a compound of formula (I) via two separate reduction steps, either the alkene moiety can be reduced first, as shown in step-3b, or the cyano group can be reduced first, as shown in step-3d.

In one embodiment of the present invention, a compound of formula (VII) is obtained from a substantially pure E-isomer of a compound of formula (I) in single reduction step-3a. One or more reducing agents can be used in step-3a and any reducing agent can be used to catalyze the reduction step in view of the present disclosure, such as hydride reagents and hydrogenation catalysts. For example, a mixture of Raney nickel and palladium on carbon can be used. If only one reducing agent is used, the reducing agent reduces both the alkene moiety and the cyano group. Reducing step-3a is also performed in the presence of hydrogen, and preferably hydrogen gas. Step-3a can also optionally be performed in the presence of an alkylating agent. The same reaction parameters described for reduction step-2a, ie. reaction time, reaction solvent, temperature, amount of reducing agent, pressure, and the alkylating reagents and conditions for the optional alkylation step can be applied to step-3a.

In a preferred embodiment, the mixture of (R,R) and (S,S) stereoisomers of the compound of formula (VII) is then separated to obtain a substantially optically pure (R,R) stereoisomer. The mixture can be separated in the same manner as described for the separation of the mixture of (R,R) and (S,S) stereoisomers of a compound of formula (V) obtained from reduction step-2a. Preferably, the mixture is separated by chromatography, more preferably by continuous chromatography, and most preferably by SMB.

In another embodiment of the present invention, a compound of formula (VII) is obtained from a substantially pure E-isomer of a compound of formula (I) in two separate reduction steps, wherein the alkene moiety is first selectively reduced to obtain a compound of formula (VI), or a pharmaceutically acceptable salt thereof, wherein $R_1$ represents a hydrogen, aliphatic, aryl, or phenolic oxygen protecting group, as shown in step-3b. Reduction step-3b is performed in the presence of hydrogen, preferably hydrogen gas, and any reducing agent in view of the present disclosure that is capable of selectively reducing the alkene moiety, but not the cyano group. "Selectively reduced" as used herein is intended to mean that only one functional group capable of undergoing a reduction reaction is reduced, while other functional groups also capable of being reduced remain unaffected. Examples of reducing agents that can be used in step-3b include, but are not limited to palladium on carbon and platinum on carbon. In a preferred embodiment, reducing step-3b is catalyzed by palladium or platinum on carbon. In a particularly preferred embodiment, reducing step-3b comprises palladium-catalyzed heterogeneous hydrogenation. For example, step-3b can be performed in the presence of 10% palladium on carbon and 50 psi of $H_2$ gas in isopropanol. A range of temperatures, pressures and reaction times can be used to selectively reduce the alkene moiety, and one skilled in the art will be readily able to optimize these parameters.

The compound of formula (VI) is then subjected to a second reduction step-3c to thereby obtain a mixture of (R,R) and (S,S) stereoisomers of a compound of formula (VII). Reducing step-3c comprises reacting the compound of formula (VI) with any reducing agent in view of the present disclosure capable of reducing the cyano group. Preferably, step-3c is carried out in the presence of a nickel catalyst, and more preferably Raney nickel or Sponge nickel. Reduction step-3c can also optionally be carried out in the presence of an alkylating agent. Any alkylating agent can be used in view of the present disclosure.

In a preferred embodiment, the mixture of (R,R) and (S,S) stereoisomers of the compound of formula (VII) obtained from step-3c is separated as described above for the product of step-2a, to obtain a substantially optically pure (R,R) stereoisomer of the compound of formula (VII). In a more preferred embodiment, the mixture of (R,R) and (S,S) stereoisomers of the compound of formula (VI) obtained from step-3b is separated to obtain a substantially optically pure (R,R) stereoisomer of the compound of formula (VI). Reducing step-3c can then be performed on the substantially optically pure (R,R) stereoisomer of the compound of formula (VI). Preferably, the separation step is carried out by chromatography, more preferably by continuous chromatography, and most preferably by SMB.

In another embodiment of the present invention, a compound of formula (VII) is obtained from a substantially pure E-isomer of a compound of formula (I) in two separate reduction steps, wherein the cyano moiety is first selectively reduced to obtain a compound of formula (IV), or a pharmaceutically acceptable salt thereof, wherein $R_1$ represents a hydrogen, aliphatic, aryl, or phenolic oxygen protecting group, and $R_5$ represents a hydrogen or alkyl, as shown in step-3d of Scheme 3 above. Reduction step-3d is performed in the presence of a reducing agent that only reduces the cyano group, and not the alkene moiety, such as, for example, a nickel catalyst, and preferably Raney nickel or Sponge nickel. A range of temperatures, pressures and reaction times can be used to selectively reduce the cyano group, and one skilled in the art will be readily able to optimize these parameters. Step-3d can also optionally be performed in the presence of an alkylating agent and any alkylating agent can be used in view of the present disclosure.

The compound of formula (IV) is then subjected to a second reduction step-3e to thereby obtain a mixture of (R,R) and (S,S) stereoisomers of a compound of formula (VII).

a mixture of (R,R) and (S,S) stereoisomers of the compound of formula (VII) obtained by reducing a substantially pure E-isomer of a compound of formula (I) in two separate reduction steps, wherein the cyano moiety is reduced first, as depicted and described for reducing step-3d, followed by reduction of the alkene moiety as depicted and described for reducing step-3e.

In another embodiment of the present invention, a substantially optically pure (R,R) stereoisomer of a compound of formula (VII) is prepared according to a method of the present invention as shown below in scheme 4:

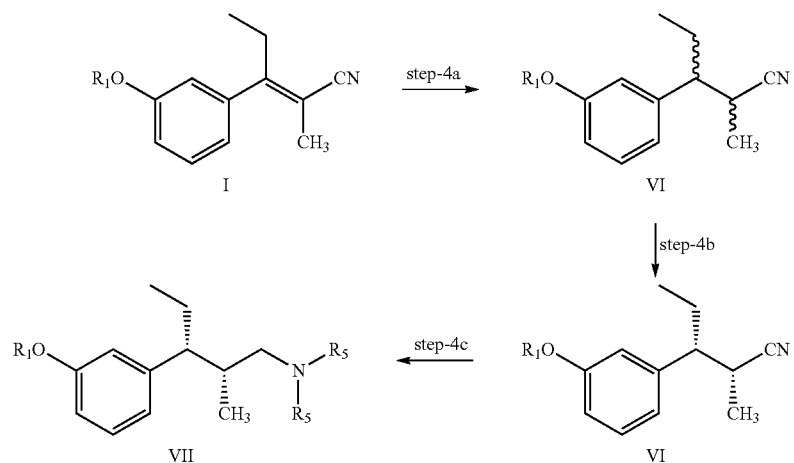

Reducing step-3e comprises reacting the compound of formula (IV) with hydrogen, preferably hydrogen gas, and any reducing agent capable of reducing the alkene moiety including, but not limited to, palladium on carbon, platinum on carbon. In a preferred embodiment, reducing step-3e is catalyzed by palladium or platinum on carbon, and preferably 10% palladium or platinum on carbon.

In a preferred embodiment, the mixture of (R,R) and (S,S) stereoisomers of the compound of formula (VII) obtained from step-3e is separated to obtain a substantially optically pure (R,R) stereoisomer of the compound of formula (VII). Preferably, the separation is carried out by chromatography, more preferably by continuous chromatography, and most preferably by SMB.

According to an embodiment of the present invention, two different metal catalysts can be used for the reduction of an alkene followed by a 1-pot/1-step reductive amination.

Another aspect of the present invention relates to a method of preparing a substantially optically pure (R,R) stereoisomer of a compound of formula (VII) or a pharmaceutically acceptable salt thereof.

In one embodiment, a substantially optically pure (R,R) stereoisomer of a compound of formula (VII) is obtained according to a method of the invention by separating a mixture of (R,R) and (S,S) stereoisomers of the compound of formula (VII) obtained by reducing a substantially pure E-isomer of a compound of formula (I) in a single reduction step to a compound of formula (VII), as depicted and described for reducing step-3a.

In another embodiment, a substantially optically pure (R,R) stereoisomer of a compound of formula (VII) is obtained according to a method of the invention by separating wherein a substantially pure E-isomer of a compound of formula (I) is reacted with a reducing agent in reducing step-4-a to selectively reduce the alkene moiety, thereby obtaining a mixture of (R,R) and (S,S) stereoisomers of a compound of formula (VI). The same reaction conditions as described for step-3b can be applied to step-4-a. Preferably the reducing agent is palladium or platinum on carbon, and more preferably 10% palladium on carbon. The mixture of stereoisomers is then separated to obtain a substantially optically pure (R,R) stereoisomer of a compound of formula (VI). Any method for separating the two stereoisomers can be used in view of the present disclosure. Preferably, the stereoisomers are separated by chromatography, more preferably by continuous chromatography, and most preferably by SMB.

The substantially optically pure (R,R) stereoisomer of a compound of formula (VI) is then reacted with a second reducing agent in a second reducing step-4-c to obtain a substantially optically pure (R,R) stereoisomer of a compound of formula (VII). Any reducing agent and suitable reaction conditions that will result in reduction of the cyano group can be used in view of the present disclosure. In a preferred embodiment, the reducing agent is a nickel catalyst, and more preferably Raney nickel. Optionally, step-4-c can also be performed in the presence of an alkylating reagent.

In a preferred embodiment, a method of the present invention produces a substantially optically pure (R,R) stereoisomer of a compound of formula (VII), or a pharmaceutically acceptable salt thereof, wherein $R_1$ represents hydrogen and $R_5$ represents methyl.

The present invention also relates to a substantially pure E-isomer of a compound according to formula (IV):

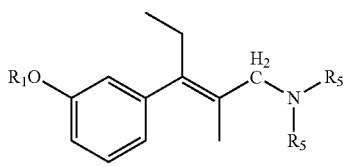

IV or a pharmaceutically acceptable salt thereof and methods for preparing the substantially pure E-isomer, wherein $R_1$ represents a hydrogen, alkyl, aryl, or silyl-protecting group, and $R_5$ represents a hydrogen or alkyl.

According to embodiments of the present invention, a method for preparing a substantially pure E-isomer of a compound of formula (IV) comprises reacting a substantially pure E-isomer of a compound of formula (I), or a pharmaceutically acceptable salt thereof, with a reducing agent and optionally an alkylating reagent in the presence of a nickel catalyst. Any reducing agent that is capable of selectively reducing the cyano group, but not the alkene moiety, can be used in view of the present disclosure, such as for example, a nickel catalyst, including Raney nickel and Sponge nickel, and preferably Raney nickel. The same reaction conditions as described above for reduction step-3d can also be used. The reduction of a compound of formula (I) to a compound of formula (IV) can also be performed in the presence of an alkylating reagent, and any alkylating reagent in view of the present disclosure can be used.

According to embodiments of the present invention, both a mixture of (R,R) and (S,S) stereoisomers, and a substantially optically pure (R,R) isomer of a compound of formula (VII) can be produced from a substantially pure E-isomer of a compound of formula (IV). A substantially pure E-isomer of a compound of formula (IV) can be reduced using any method in view of the present disclosure for reducing an alkene moiety to obtain a mixture of (R,R) and (S,S) stereoisomers of a compound of formula (IV). Preferably, the reduction step is carried out in the presence of palladium on carbon or platinum on carbon. A substantially optically pure (R,R) isomer can thus be obtained by separating the (R,R) and (S,S) stereoisomers in the mixture. Any method for separating the (R,R) and (S,S) stereoisomers can be used, and the method of separation preferably comprises chromatography, more preferably continuous chromatography, and even more preferably SMB.

The following examples of methods for preparing 3-phenyl-2-methylpent-2-enenitrile and 3-(1-amino-2-methylpentane-3-yl)phenyl compounds according to embodiments of the present invention are to further illustrate the nature of the invention. It should be understood that the following examples do not limit the invention and that the scope of the invention is determined by the appended claims.

EXAMPLES

The following abbreviations are used in the following examples, unless clearly stated otherwise:
$^1$H NMR: proton nuclear magnetic resonance
THF: tetrahydrofuran
EtOAc: ethyl acetate
HPLC: high performance liquid chromatography
$^{13}$C NMR: carbon nuclear magnetic resonance
m.p.: melting point
LC-MS: liquid chromatography mass spectrometry
TLC: thin layer chromatography
IPA: isopropyl alcohol
DEA: diisopropylethylamine
e.e.: enantiomeric excess
d.e.: diastereomeric excess Example 1

Preparation of (E)-3-(3-methoxyphenyl)-2-methyl-pent-2-enenitrile using sodium hydride Sodium hydride (0.51 g, 12.8 mmol) was suspended in anhydrous THF (20 mL) under a nitrogen ($N_2$) atmosphere, and the suspension was cooled to 5° C. in an ice bath. After 10 min, diethyl 1-cyanoethylphosphonate (2.44 g, 12.8 mmol) in THF (5 mL) was added slowly drop by drop over about 5 min. After 15 min at 5° C., 3-methoxy propiophenone (2.0 g, 12.12 mmol) in THF (5 mL) was added slowly drop-wise over 5 min. The reaction mixture was then slowly warmed to room temperature and stirred for 3 h. The reaction mixture was heated to reflux (65° C.) for about 12 h. The reaction mixture was cooled to 0° C., quenched with saturated aq. $NH_4Cl$ solution (20 mL), and then THF was evaporated under reduced pressure. The resulting aqueous layer was extracted with EtOAc (3×25 mL), the organic layers were combined, washed with water (25 mL), brine solution (25 mL), dried over anhydrous $Na_2SO_4$ and evaporated under reduced pressure generating 2.55 g of a brownish oil. Separation of the isomers was accomplished by silica gel flash column chromatography (~50.0 g $SiO_2$, eluent 2% to 5% EtOAc/hexanes). The separated isomers were characterized by $^1$H NMR.

The E-isomer was obtained as a pale yellow oil (1.61 g, 65.0%); $^1$H NMR (CDCl$_3$, 400 MHz): δ 0.98 (t, J=7.5 Hz, 3H), 1.79 (t, J=0.96 Hz, 3H), 2.73 (qq, J=7.5, 0.98 Hz, 2H), 3.82 (s, 3H), 6.62-6.63 (m, 1H), 6.66-6.69 (m, 1H), 6.85-6.89 (m, 1H), 7.26-7.33 (m, 1H).

The Z-isomer was obtained as a pale yellow oil (0.4 g, 16.0%); $^1$H NMR (CDCl$_3$, 400 MHz): δ 0.96 (t, J=7.5 Hz, 3H), 2.06 (s, 3H), 2.52 (q, J=7.5 Hz, 2H), 3.82 (s, 3H), 6.83-6.84 (m, 1H), 6.88-6.89 (m, 1H), 6.90-6.91 (m, 1H), 7.28-7.32 (m, 1H).

Example 2

Preparation of (E)-3-(3-methoxyphenyl)-2-methyl-pent-2-enenitrile using potassium tert-butoxide Potassium tert-butoxide (3.27 g, 29.3 mmol) was dispersed in anhydrous THF (20 mL) under $N_2$ atmosphere, and the resulting mixture cooled to 5° C. in an ice bath. After 10 min, diethyl-cyanoethylphosphonate (3.25 g, 17.0 mmol) in THF (5 mL) was added drop-wise over 5 min. After 15 min at 5° C., 3-methoxy propiophenone (2.0 g, 12.18 mmol) in THF (5 mL) was added drop-wise over about 5 min. The reaction mixture was slowly warmed to room temperature where it was maintained for 16 h. The reaction was quenched with water (15 mL), THF was evaporated under reduced pressure, and the resulting aqueous layer was neutralized with aqueous 3N HCl (10 mL). The aqueous layer was then extracted with EtOAc (3×25 mL), and the organic layers were combined, washed with brine solution (25 mL), dried over anhydrous $Na_2SO_4$ and evaporated under reduced pressure producing 2.53 g of a brownish oil. Separation of the isomers was accomplished by silica gel flash column chromatography (~50 g $SiO_2$, eluent 2% to 5% EtOAc/hexanes).

The E-isomer was obtained in 63% yield (1.54 g) and the Z-isomer was obtained in 18% yield (0.43 g). The isomers were characterized by $^1$H NMR, with the $^1$H NMR data being in good agreement with that reported for Example 1.

Example 3

Demethylation of (E)-3-(3-methoxyphenyl)-2-methylpent-2-enenitrile to produce (E)-3-(3-hydroxyphenyl)-2-methylpent-2-enenitrile (E)-3-(3-methoxyphenyl)-2-methylpent-2-enenitrile (0.50 g, 2.48 mmol) was dissolved in $CH_2Cl_2$ (5 mL) under $N_2$ atmosphere and the resulting solution was cooled to 5° C. (ice bath). A solution of $BBr_3$ (0.352 mL, 3.72 mmol) in $CH_2Cl_2$ (5 mL) was added drop-wise, after which the ice bath was removed. After 5 h at room temperature, the mixture was cooled to 5° C. and diluted with $CH_2Cl_2$ (15 mL), quenched with water (20 mL) and the layers were separated. The separated aqueous layer was extracted with $CH_2Cl_2$ (2×25 mL) and the organic layers were combined, washed with brine solution (25 mL), dried over $Na_2SO_4$, filtered and concentrated under reduced pressure.

The resulting residue was twice dissolved in MeOH (15 mL) and concentrated under reduced pressure to produce 0.46 g (99%) of (E)-3-(3-hydroxyphenyl)-2-methylpent-2-enenitrile as a dark brown solid. MP: 80-83° C.; $^1$H NMR consistent with that reported below for (E)-3-(3-hydroxyphenyl)-2-methylpent-2-enenitrile in Examples 4 and 5.

Example 4

Preparation of (E)-3-(3-hydroxyphenyl)-2-methylpent-2-enenitrile using sodium hydride Sodium hydride (1.17 g, 29.3 mmol) was dispersed in anhydrous THF (20 mL) under $N_2$ atmosphere, and the suspension was cooled to 5° C. in an ice bath. After 10 min diethyl 1-cyanoethylphosphonate (3.05 g, 16.0 mmol) in THF (5 mL) was added drop by drop over 5 min. After 15 min at 5° C., 3-hydroxy propiophenone (2.0 g, 13.3 μmol) in THF (5 mL) was added drop-wise over 5 min. The ice bath was then removed and slowly the reaction mixture warmed to room temperature where it was maintained for 4 h. The reaction was monitored by TLC and because TLC indicated unreacted starting material was still present, the reaction mixture was heated up to 55° C. (internal) for 3 h. The reaction was cooled to room temperature, quenched with saturated aq. $NH_4Cl$ solution (20 mL), THF was removed under reduced pressure, and the aqueous layer was extracted with EtOAc (3×25 mL). The combined organic layer was washed with brine solution (25 mL), dried over anhydrous $Na_2SO_4$ and concentrated under reduced pressure providing a brownish oil (2.7 g). The isomers were separated by flash column chromatography (~50.0 g $SiO_2$, eluent 5% to 10% EtOAc/hexanes).

The E-isomer was recrystallized from $CH_2Cl_2$: hexanes 1:2 (30 mL) as a white solid (1.04 g, 42.0%), and characterized by $^1$H NMR (see $^1$H NMR data in Example 5 below). The Z-isomer was obtained as a pale yellow oil (0.56 g, 22.0%), and characterized by $^1$H NMR (see $^1$H NMR data in Example 5 below).

Example 5

Preparation of (E)-3-(3-hydroxyphenyl)-2-methylpent-2-enenitrile using potassium tert-butoxide Potassium tert-butoxide (206.8 g, 1.844 mol) was dispersed in anhydrous THF (700 mL) under $N_2$ atmosphere, in a three-necked-round-bottom flask (3 ) equipped with an internal thermometer, was cooled to 5° C. in an ice bath. After 10 min, diethyl 1-cyanoethylphosphonate (130.0 g, 0.68 mol) in THF (200 mL) was added drop by drop via a dropping funnel over 30 min. After 15 min at 5° C., 3-hydroxy propiophenone (72.90 g, 0.486 mol) in THF (200 mL) was added drop-wise via an addition funnel over 30 min. Then the reaction mixture was slowly warmed to room temperature and stirred for 16 h. The reaction mixture was heated to reflux (65° C. internal) for 3 h. After 3 h, the reaction mixture was cooled to room temperature, quenched with water (200 mL), THF removed under reduced pressure, and neutralized with aqueous 3N HCl (180 mL). The resulting aqueous layer was extracted with EtOAc (3×300 mL), and the combined organic layer was washed with brine solution (200 mL), dried over anhydrous $Na_2SO_4$ and evaporated under reduced pressure producing a brownish oil (140.0 g). Purification was accomplished by flash column chromatography (1.5 kg $SiO_2$, elutent with 5% to 10% EtOAc/hexanes). Liquid chromatography was repeated 2 more times to separated 3-hydroxypropiophenone starting material from the E-isomer (0.5 kg $SiO_2$ and 0.3 kg $SiO_2$). The collected white solid of the E-isomer was recrystallised from $CH_2Cl_2$: hexanes ~1:2 (150 mL).

The E-isomer was obtained as a white solid (32.23 g, 35.0%); a further 10.0 g mixture of the E-isomer and unreacted 3-hydroxypropiophenone was also isolated. TLC: $R_f$ 0.55 (25% EtOAc:hexanes); MP: 87-89° C.; $_1$H NMR ($CDCl_3$, 400 MHz): δ 0.97 (t, J=7.5 Hz, 3H), 1.80 (t, J=0.92 Hz, 3H), 2.71 (qq, J=7.5, 0.92 Hz, 2H), 5.13-5.27 (br.s, 1H), 6.58-6.59 (m, 1H), 6.64-6.66 (m, 1H), 6.80-6.83 (m, 1H), 7.23-7.27 (m, 1H); $^{13}$C NMR ($CDCl_3$, 100 MHz): δ 12.5, 17.4, 31.5, 104.3, 114.3, 115.3, 119.4 (2 C), 129.7, 138.9, 156.0, 161.2 ppm; LCMS: 188.1 (M+H); HPLC: 99.93% purity (254 nm).

The Z-isomer was obtained as a pale yellow oil (16.38 g, 18.0%); a further 7.0 g mixture of the Z-isomer and unreacted 3-hydroxypropiophenone was also isolated. TLC: $R_f$: 0.40 (25% EtOAc:hexanes); $^1$H NMR ($CDCl_3$, 400 MHz): δ 0.94 (t, J=7.5 Hz, 3H), 2.05 (s, 3H), 2.50 (q, J=7.5 Hz, 2H), 6.77-6.81 (m, 2H), 6.83-6.86 (m, 1H), 7.20-7.24 (m, 1H); $^{13}$C NMR ($CDCl_3$, 100 MHz): δ 11.7, 16.6, 27.0, 104.2, 114.5, 115.8, 119.6, 120.2, 129.5, 140.8, 155.8, 161.2 ppm; LCMS: 188.1 (M+H); HPLC: 98.6% purity (254 nm).

Example 6

Isomerization of (Z)-3-(3-methoxyphenyl)-2-methylpent-2-enenitrile to (E)-3-(3-methoxyphenyl)-2-methylpent-2-enenitrile using potassium tert-butoxide (Z)-3-(3-Methoxyphenyl)-2-methylpent-2-enenitrile (0.26 g, 0.99 mmol) was dissolved in anhydrous THF (3 mL), and the resulting solution cooled to 5° C. in an ice bath, after which potassium tert-butoxide (KOtBu) (0.022 g, 0.19 mmol) was added in one portion. The ice bath was removed and the resulting mixture was warmed to room temperature where it was maintained overnight (TLC indicated ~20% isomerisation). The solution was cooled to 5° C. and additional KOtBu (0.115 g, 0.794 mmol, 0.8 equivalents) was added. After 6 h at room temperature, the reaction was quenched with water (5 mL) and the THF was removed under reduced pressure.

The resulting aqueous solution was neutralized (pH ~7) with 3N HCl (5 mL), extracted with EtOAC (3×15 mL), and the combined organic layer was washed with brine solution (10 mL), dried over $Na_2SO_4$, and concentrated under reduced pressure to provide 0.23 g of a brown oil. The isomerization reaction yielded 76% conversion of the Z-isomer to the E-isomer as indicated by $^1$H NMR characterization of the crude product (ratio cis:trans (Z:E) of 1.0:3.2; 76% conversion).

Example 7

Isomerization of (Z)-3-(3-hydroxyphenyl)-2-methylpent-2-enenitrile to (E)-3-(3-hydroxyphenyl)-2-methylpent-2-enenitrile using potassium tert-butoxide (Z)-3-(3-Hydroxyphenyl)-2-methylpent-2-enenitrile (27.0 g, 144.2 mmol) was dissolved in anhydrous THF (270 mL) and after cooling to 5° C. in an ice bath potassium tert-butoxide (32.33 g, 288.4 mmol) was added in one portion. The resulting mixture was slowly warmed to room temperature and then heated to reflux. After 3 h, the reaction was cooled to room temperature and quenched with water (50 mL), and the THF was removed under reduced pressure. The resulting aqueous layer was neutralized (to pH ~7) with 3N HCl (35 mL), and extracted with EtOAc (3×200 mL). The organic layers were combined, washed with brine solution (150 mL), dried over $Na_2SO_4$, and concentrated under reduced pressure generating 28.0 g of a brown oil.

The isomers were separated by flash column chromatography (~300.0 g $SiO_2$, eluent: 5% to 12% EtOAc:hexanes). The E-isomer was recrystallized from $CH_2Cl_2$:hexanes 1:2 (75 mL) as a white crystalline solid (12.0 g; 44%). The Z-isomer was obtained as a pale yellow oil (8.12 g; 30%).

Example 8

Preparation of (±)-3-(3-Hydroxyphenyl)-2-methylpentanenitrile (mixture of (R,R) and (S,S) stereoisomers) from reduction of (E)-3-(3-hydroxyphenyl)-2-methylpent-2-enenitrile (E)-3-(3-hydroxyphenyl)-2-methylpent-2-enenitrile (6.06 g, 32.4 mmol) was dissolved in 2M $NH_3$/IPA (80 mL) in a steel reactor equipped with a magnetic stir bar. 10% Pd/C (53% wet) (1.5 g) was added. The reactor was sealed, and purged with $N_2$ (3×~30 psi) and $H_2$ (3×~30 psi). The reaction was stirred at room temperature at 500 rpm under $H_2$ (50 psi) for 22 h, whereupon the calculated amount of unreacted starting material was <2%, as determined by HPLC. The reaction mixture was filtered through a Celite pad which was washed with toluene (50 mL). The filtrate was evaporated and then coevaporated with toluene (50 mL) to remove remaining traces of IPA. The residue was dissolved in toluene (50 mL) which was passed through a $SiO_2$ column (Grace Davison 633) (20 g).

The column was eluted with 2% EtOH/toluene (300 mL), and fractions containing the product (as determined by TLC) were combined and evaporated (4.94 g, 80.6%; 97.4% de; m/z 190 (M+1); $^1$H NMR (CDCl$_3$) δ 0.81 (t, 3H), 1.16 (d, 3H), 1.83 (quin, 2H), 2.51 (q, 1H), 2.94 (quin, 1H), 5.91 (bs, 1H), 6.76-6.82 (m, 3H), 7.14-7.22 (m, 1H); $^{13}$C NMR (CDCl$_3$) δ 12.00, 16.22, 26.36, 31.12, 49.71, 114.48, 114.91, 120.91, 121.95, 129.67, 141.36, 155.91.

Example 9

Preparation of (±)-3-(1-(dimethylamino)-2-methylpentan-3-yl)phenol (mixture of (R,R) and (S,S) stereoisomers) from reduction and alkylation of (±)-3-(3-hydroxyphenyl)-2-methylpentanenitrile Crude (±)-3-(3-hydroxyphenyl)-2-methylpentanenitrile (4.82 g, 25.4 mmol) and 37% formaldehyde (8.8 mL, 118 mmol) were dissolved in MeOH (100 mL) in a stainless steel reactor equipped with a magnetic stir bar. Raney Nickel®2800 slurry (10 mL of a well shaken slurry) was added to the mixture in one portion. The reactor was purged with $N_2$ (3×~30 psi) and $H_2$ (3×~40 psi). The reactor was then charged with $H_2$ (50 psi) and stirred at 750 rpm at room temperature. After 25.75 h stirring, the reaction was incomplete as determined by HPLC, and a second portion of Raney Nickel® (3 mL) and 37% formaldehyde (3 mL) was added to the reaction and stirring continued for a further 18 h. The reactor was opened and the contents were filtered under $N_2$ through a Celite pad which was then washed with MeOH (50 mL). Water (50 mL) and conc. $H_2SO_4$ (3 mL, 54 mmol) were added to the filtrate which was then subjected to rotary evaporation to remove MeOH. The residue was extracted with $CH_2Cl_2$ (2×25 mL) which was discarded. The aqueous layer was made basic with $Na_2CO_3$ (7 g, 66 mmol) and extracted with $CH_2Cl_2$ (2×50 mL).

The combined $CH_2Cl_2$ extracts were dried ($Na_2SO_4$), filtered and evaporated to get an oil which slowly solidified (4.65 g, 82.6%): m/z 222 (M+1); $^1$H NMR (CDCl$_3$) δ 0.67 (t, 3H), 0.95 (d, 3H), 1.42-1.58 (m, 1H), 1.64-1.76 (m, 1H), 1.76-1.94 (m, 1H), 2.02-2.18 (m, 2H), 2.16 (s, 6H), 2.20-2.30 (m, 1H), 6.54 (t, 1H), 6.60 (m, 1H), 6.62 (m, 1H), 7.07 (t, 1H), 7.51 (bs, 1H); $^{13}$C NMR (CDCl$_3$) 12.26, 16.05, 23.80, 36.39, 45.49, 51.33, 64.62, 113.28, 115.64, 120.11, 129.10, 145.78, 156.41.

Example 10

Preparation of (±)-3-(1-(dimethylamino)-2-methylpentan-3-yl)phenol (mixture of (R,R) and (S,S) stereoisomers) from reduction and alkylation of (±)-3-(3-hydroxyphenyl)-2-methylpentanenitrile Crude (±)-3-(3-hydroxyphenyl)-2-methylpentanenitrile (7.7 g, 41.1 mmol) and 37% aqueous formaldehyde (25 mL, 340 mmol) were dissolved in MeOH (20 mL) in a stainless steel Parr reactor. Sponge nickel (J&M A5000) slurry (16.4 g of solid) was washed with water (3×25 mL) and MeOH (3×25 mL), decanting the supernatant liquid after each wash. The nickel slurry was transferred into the reactor using MeOH (155 mL) for a total reaction volume of 200 mL. The reactor was sealed, purged with $N_2$ (3×50 psi) and $H_2$ (3×50 psi) and then charged with $H_2$ (50 psi). The reaction mixture was stirred (500 rpm) under $H_2$ (50 psi) at room temperature. HPLC analysis at 40 h indicated incomplete reaction. Further portions of sponge nickel (5.2 g) and 37% formaldehyde 5 mL) were added and stirring continued. After a total of 48.5 h HPLC indicated complete consumption of starting material. The reactor contents were passed through a Celite 545 column (10 g) which was washed with MeOH (150 mL). The combined filtrate was evaporated to remove MeOH. The resulting cloudy oil was partitioned between $CH_2Cl_2$ (50 mL) and 1.8 M $H_2SO_4$ (100 mL), and the aqueous layer was washed with a further portion of $CH_2Cl_2$ (50 mL). The acidic aqueous layer was neutralized with $Na_2CO_3$ (24 g in 100 mL water) to give a cloudy mixture which was extracted with $CH_2Cl_2$ (2×50 mL). The combined $CH_2Cl_2$ extracts were dried ($Na_2SO_4$), filtered and evaporated to obtain a viscous yellow oil (7.9 g, 86.6%; 95.65% de): m/z 222; $^1$H NMR (CDCl$_3$) δ 0.67 (t, 3H), 0.95 (d, 3H), 1.42-1.60 (m, 1H), 1.64-1.78 (m, 1H), 1.78-1.94 (m, 1H), 2.02-2.18 (m, 2H), 2.16 (s, 6H), 2.20-2.32 (m, 1H), 6.54 (m, 1H), 6.60 (m, 1H), 6.62 (m, 1H), 7.09 (t, 1H); $^{13}$C NMR (CDCl$_3$) δ 12.39, 16.18, 23.93, 36.56, 45.66, 51.51, 64.81, 113.41, 115.81, 120.25, 129.19, 145.96, 156.57.

Example 11

Preparation of optically pure (2R,3R)-3-(1-(dimethylamino)-2-methylpentan-3-yl)phenol (tapentadol) from (±)-3-(1-(dimethylamino)-2-methylpentan-3-yl)phenol by simulated moving bed chromatography Crude (±)-3-(1-(dimethylamino)-2-methylpentan-3-yl)phenol (11.44 g, 51.7 mmol) was subjected to resolution by simulated moving bed chiral chromatography. Separation was achieved with eight 1.0×10 cm columns packed with 20 µm Chiralcel OJ chiral stationary phase. The eluent composition was 5% IPA/heptane/0.2% DEA and the separation was run at ambient temperature.

The (R,R) stereoisomer was collected in the raffinate stream and the (S,S) stereoisomer was collected in the extract stream. The desired product was collected and concentrated to provide: (R,R) stereoisomer (3.31 g, 29.7%); ee, 99.6%, de, 58.0%; $^1$H NMR (MeOH, d$_4$) δ 0.71 (t, 3H), 0.98 (d, 2H), 1.46-1.64 (m, 1H), 1.64-1.92 (m, 3H), 2.0-2.1 (m, 2H), 2.10 (s, 6H), 2.15-2.26 (m, 1H), 6.59 (d, 3H), 7.07 (t, 1H); $^{13}$C NMR (MeOH d$_4$) δ 12.68, 16.70, 25.49, 37.70, 53.12, 66.12, 113.95, 116.26, 120.88, 130.08, 146.91, 158.37; (S,S) stereoisomer (3.8 g, 33.4%); ee, 97.4%, $^1$H NMR (CDCl$_3$) δ 0.61 (t, 3H), 0.90 (d, 2H), 1.38-1.54 (m, 1H), 1.58-1.72 (m, 1H), 1.74-1.89 (m, 1H), 1.96-2.1 (m, 2H), 2.10 (s, 6H), 2.14-2.26 (m, 1H), 6.50 (m, 1H), 6.54 (m, 1H), 6.56 (m, 1H), 7.03 (t, 1H).

Example 12

Preparation of an (2R,3R)-3-(1-(dimethylamino)-2-methylpentan-3-yl)phenol (tapentadol) from (±)-3-(1-(dimethylamino)-2-methylpentan-3-yl)phenol by SMB chromatography.

Crude (±)-3-(1-(dimethylamino)-2-methylpentan-3-yl)phenol (9.79 g, 51.7 mmol) was subjected to resolution by simulated moving bed chiral chromatography. Separation was achieved with eight 1.0 ×10 cm columns packed with 20 µm Chiralcel OJ chiral stationary phase. The eluent composition was 5%/95% IPA/n-heptane +0.2% DEA and the separation was run at ambient temperature.

The (R,R) stereoisomer was collected in the raffinate stream and the (S,S) stereoisomer was collected in the extract stream. The desired product was collected and concentrated to provide: (R,R) stereoisomer (4.16 g, 42.5%); ee, 99.6%, de, 86.0%; $^1$H NMR (CDCl$_3$) δ 0.62 (t, 3H), 0.90 (d, 2H), 1.38-1.54 (m, 1H), 1.58-1.72 (m, 1H), 1.74-1.86 (m, 1H), 1.96-2.1 (m, 2H), 2.10 (s, 6H), 2.14-2.26 (m, 1H), 6.50 (m, 1H), 6.55 (m, 1H), 6.57 (m, 1H), 7.03 (t, 1H); (S,S) stereoisomer (3.91 g, 39.9%); ee, 91.8%; de, 98.6%.

Example 13

Preparation of an (2R,3R)-3-(1-(dimethylamino)-2-methylpentan-3-yl)phenol (tapentadol) from (±)-3-(1-(dimethylamino)-2-methylpentan-3-yl)phenol by SMB chromatography.

Crude (±)-3-(1-(dimethylamino)-2-methylpentan-3-yl)phenol (23.82 g, 108 mmol) was subjected to resolution by simulated moving bed chiral chromatography. Separation was achieved with eight 1.0 ×10 cm columns packed with 20 µm Chiralcel OJ chiral stationary phase. The eluent composition was 5%/95% IPA/n-heptane +0.2% DEA and the separation was run at ambient temperature.

The (R,R) stereoisomer was collected in the raffinate stream and the (S,S) stereoisomer was collected in the extract stream. The products were collected and concentrated to provide: (R,R) stereoisomer (11.28 g, 47.4%); ee, >99%, de, 91.76%; $^1$H NMR (CDCl$_3$) δ 0.67 (t, 3H), 0.96 (d, 3H), 1.44-1.58 (m, 1H), 1.64-1.78 (m, 1H), 1.80-1.94 (m, 1H), 2.08-2.18 (m, 2H), 2.16 (s, 6H), 2.20-2.30 (m, 1H), 6.50 (m, 1H), 6.57 (m, 1H), 6.61 (m, 1H), 7.08 (t, 1H); $^{13}$C NMR (CDCl$_3$) δ 12.23, 16.10, 23.90, 36.34, 45.44, 51.43, 64.67, 113.40, 115.74, 119.93, 129.03, 145.68, 156.69; (S,S) stereoisomer (11.09 g, 46.6%); ee, 79.74%; de, 97.22%; $^1$H NMR (CDCl$_3$) δ 0.62 (t, 3H), 0.90 (d, 3H), 1.36-1.54 (m, 1H), 1.58-1.74 (m, 1H), 1.74-1.88 (m, 1H), 1.96-2.08 (m, 2H), 2.10 (s, 6H), 2.14-2.28 (m, 1H), 6.50 (m, 1H), 6.54 (m, 1H), 6.57 (m, 1H), 7.03 (t, 1H), 7.35 (bs, 1H); $^{13}$C NMR (CDCl$_3$) δ 12.25, 16.07, 23.82, 36.41, 45.49, 51.36, 64.67, 113.35, 115.70, 120.05, 129.05, 145.77, 156.58.

Example 14

Conversion of (2R,3R)-3-(1-(dimethylamino)-2-methylpentan-3-yl)phenol to (2R,3R)-3-(1-(dimethylamino)-2-methylpentan-3-yl)phenol hydrochloride Crude (2R,3R)-3-(1-(dimethylamino)-2-methylpentan-3-yl)phenol (489 mg, 2.21 mmol)) (de 58.0%) was dissolved in IPA (5 mL) at room temperature to get a pale yellow solution. 4M HCl/dioxane was added (0.55 mL, 2.20 mmol) rapidly via a syringe and stirred at room temperature. After ~0.5 h a white solid precipitated. The mixture was heated to reflux to get a clear solution and then allowed cool to room temperature and precipitate over a period of 3 h. The mixture was cooled briefly (0.5 h) in an ice bath, filtered, and the solid was washed with cold IPA (1 mL), then cold iPrOAc (1 mL) and air dried to get a white solid: (389 mg, 68.6%; de, 86.4%); $^1$H NMR (MeOH d$_4$) δ0.72 (t, 3H), 1.14 (d, 3H), 1.52-1.68 (m, 1H), 1.82-1.96 (m, 1H), 2.10-2.22 (m, 1H), 2.22-2.32 (m, 1H), 2.7-2.8 (bm, 6H), 2.8-2.94 (m, 2H), 4.88 (s, 2H), 6.66 (m, 3H), 7.15, (t, 1H); $^{13}$C NMR (MeOH d$_4$) δ 12.43, 16.09, 26.17, 35.71, 52.50, 64.26, 114.79, 116.22, 130.79, 145.00, 158.91.

Example 15

Conversion of (2R,3R)-3-(1-(dimethylamino)-2-methylpentan-3-yl)phenol to (2R,3R)-3-(1-(dimethylamino)-2-methylpentan-3-yl)phenol hydrochloride Crude (2R,3R)-3-(1-(dimethylamino)-2-methylpentan-3-yl)phenol (7.29 g, 32.9 mmol)) (de 93.07%) was dissolved in IPA (36 mL) at 70° C. to get a pale yellow solution. 4M HCl/dioxane (8.4 mL, 33.6 mmol) was added over a 5 minute period. A white solid precipitated after ~5 minutes. The mixture was stirred at 70° C. for 1.5 h and then allowed cooled to room temperature overnight (16 h). The slurry was placed in an ice bath and stirred for 2 h. The mixture was then filtered while cold and the filter cake washed with cold IPA (6 mL) and cold iPrOAc (6 mL). The white filter cake was dried under vacuum (6.85 g, 80.7%; de 97.53%): $^1$H NMR (MeOH d$_4$) δ0.72 (t, 3H), 1.15 (d, 3H), 1.50-1.68 (m, 1H), 1.80-1.96 (m, 1H), 2.10-2.22 (m, 1H), 2.22-2.32 (m, 1H), 2.73 (s, 3H), 2.81 (s, 3H), 2.78-2.94 (m, 2H), 4.81 (s, 2H), 6.62-6.70 (m, 3H), 7.15, (t, 1H); $^{13}$C NMR (MeOH d$_4$) δ 12.43, 16.09, 26.13, 35.72, 42.16, 45.90, 52.66, 114.79, 116.22, 120.54, 130.77, 145.00, 158.88.

Example 16

Phenolic Oxygen Protection of (E)-3-(3-hydroxyphenyl)-2-methylpent-2-enenitrile to obtain (E)-3-(3-(tert-Butyldimethylsilyloxy)phenyl)-2-methylpent-2-enenitrile (E)-3-(3-hydroxyphenyl)-2-methylpent-2-enenitrile (2.01 g, 10.75 mmol) was dissolved in CH$_2$Cl$_2$ (50 mL) and stirred at room temperature. Solid TBDMS-Cl (3.2 g, 21.2 mmol) was quickly added in portions. Solid imidazole (1.55 g, 22.7 mmol) was added quickly in portions, and a dense white precipitate formed. The reaction was stirred at room temperature for 27 h.

The reaction mixture was then extracted successively with water (50 mL), 1 M HCl (50 mL), water (50 mL), satd. NaHCO3 (50 mL), and satd. NaCl (50 mL). The organic layer was dried using Na$_2$SO$_4$, filtered and evaporated to obtain a mobile colorless liquid (3.85 g, >100%): m/z 302 (M+1); $^1$H NMR (CDCl$_3$) δ 0.20 (s, 6H), 0.90 (t, 3H), 0.99 (s, 9H), 1.79 (s, 3H), 2.71 (q, 2H), 6.56 (m, 1H), 6.68 (dm, 1H), 6.82 (dm, 1H), 7.25 (t, 1H).

Example 17

Preparation of (±)-3-(3-(tert-butyldimethylsilyloxy) phenyl)-2-methylpentanenitrile (mixture of (R,R) and (S,S) stereoisomers) from reduction of (E)-3-(3-(tert-Butyldimethylsilyloxy)phenyl)-2-methylpent-2-enenitrile (E)-3-(3-(tert-Butyldimethylsilyloxy)phenyl)-2-methylpent-2-enenitrile. (7.32 g, 24.3 mmol) was dissolved in iPrOAc (160 mL) in a steel reactor equipped with a magnetic stir bar. Then, 10% Pd/C (53% wet) (3.0 g, 19% w/w dry) was added. The reactor was purged with N$_2$ (3 times at ~40 psi) and H$_2$ (3 times at ~40 psi). The reactor was charged with H$_2$ (45 psi) and stirred at room temperature overnight.

The reactor contents were filtered through a Celite pad, which was washed with EtOAc. The filtrate was extracted successively with water (100 mL), 1 M HCl (100 mL), water (50 mL), satd. NaHCO$_3$ (50 mL), and satd. NaCl (25 mL). The organic layer was dried over Na$_2$SO$_4$, filtered and evaporated to obtain a mobile colorless liquid (7.65 g): m/z 304 (M+1); $^1$H NMR (CDCl$_3$) δ 0.20 (s, 6H), 0.84 (t, 3H), 0.98 (s, 9H), 1.17 (d, 3H), 1.85 (quin, 2H) 2.51 (dt, 2H), 2.93 (dq, 1H), 6.76 (d, 1H), 6.78 (dt, 1H), 6.85 (td, 1H), 7.19 (dd, 1H); $^{13}$C NMR (CDCl$_3$) δ −4.42, 12.03, 16.28, 18.21, 25.67, 26.37, 31.13, 46.77, 119.19, 120.04, 121.53, 121.81, 129.45, 141.23, 155.76.

Example 18

Preparation of (±)-3-(3-(tert-butyldimethylsilyloxy) phenyl)-N,N,2-trimethylpentan-1-amine (mixture of (R,R) and (S,S) stereoisomers) from reduction and alkylation of (±)-3-(3-(tert-butyldimethylsilyloxy) phenyl)-2-methylpentanenitrile 3-(3-(tert-butyldimethylsilyloxy)phenyl)-2-methylpentanenitrile (7.12 g, 23.6 mmol) was dissolved in MeOH (100 mL) in a steel reactor equipped with a magnetic stir bar. A well-shaken slurry of Raney®-Nickel 2800 (5 mL) was added, followed by addition of 37% formaldehyde (6 mL, 80.6 mmol). The reactor was purged with N$_2$ (3 times at ~40 psi) and H$_2$ (3 times at ~40 psi). The reactor was charged with H$_2$ (45 psi) and stirred at room temperature overnight. After 19 h a second portion of Raney®-Nickel 2800 (5 mL) was added, and stirring continued. After 43 h a third portion of Raney®-Nickel 2800 (2 mL) and 37% formaldehyde (2 mL, 26.8 mmol) was added. After 47 h the reaction was stopped and the cloudy supernatant was passed through a Celite column. The Raney®-Nickel residue was digested with MeOH, which was also passed through the Celite column, which was further washed with MeOH (~200 mL total). The MeOH was removed and the cloudy aqueous residue was partitioned between water (100 mL) and CH$_2$Cl$_2$ (100 mL). The organic layer was extracted with 1M HCl (2×50 mL), satd. NaHCO$_3$ (50 mL), and satd. NaCl (50 mL). The organic layer was dried (Na$_2$SO$_4$), filtered and evaporated to obtain a slightly viscous colorless liquid which was dried under vacuum overnight (6.70 g; 85.1%): m/z 336 (M+1); $^1$H NMR (CDCl$_3$) δ 0.18 (s, 6H), 0.71 (t, 3H), 0.98 (s and t, 12H), 155-1.9 (m, 1H), 1.7-1.9 (m, 2H), 1.95 (dd, 1H), 2.11 (s, 6H), 2.26 (m, 1H), 6.61 (t, 1H), 6.67 (dm, 1H), 6.72 (dm, 1H), 7.12 (t, 1H); $^{13}$C NMR (CDCl$_3$) δ −4.38, 12.30, 15.84, 18.23, 36.80, 45.80, 51.57, 64.86, 117.61, 120.13, 128.80, 146.26, 155.38.

Example 19

Preparation of (±)-3-(3-(tert-butyldimethylsilyloxy) phenyl)-N,N,2-trimethylpentan-1-amine (mixture of (R,R) and (S,S) stereoisomers) from reduction and alkylation of (±)-3-(3-(tert-butyldimethylsilyloxy) phenyl)-2-methylpentanenitrile (±)-3-(3-(tert-butyldimethylsilyloxy)phenyl)-2-methylpentanenitrile (3.52 g, 11.6 mmol) was dissolved in MeOH (100 mL) in a steel reactor equipped with a magnetic stir bar. A well-shaken slurry of Raney®-Nickel 2800 (8 mL) was added, followed by addition of 37% formaldehyde (8.6 mL, 115 mmol). The reactor was purged with N$_2$ (3 times at ~40 psi) and H$_2$ (3 times at ~40 psi). The reactor was charged with H$_2$ (45 psi) and stirred at room temperature. After 49.25 h the reaction was stopped and the cloudy supernatant was passed through a Celite column, which was then washed with MeOH (50 mL) and water (25 mL). Conc. H$_2$SO$_4$ (3 mL) was added to the combined eluate and the mixture stirred at room temperature. When hydrolysis was complete the reaction mixture was diluted with water (50 mL) and the MeOH removed by rotary evaporation. The residue was extracted with CH$_2$Cl$_2$ (50 mL, 20 mL). The aqueous layer was made basic with Na$_2$CO$_3$ (7.5 g, 70.8 mmol) and extracted with two portions of CH$_2$Cl$_2$ (2×50 mL). The combined organic extracts were dried (Na$_2$SO$_4$), filtered and evaporated to yield a viscous almost colorless oil (2.27 g, 88.3%): m/z 222 (M+1); $^1$H NMR (CDCl$_3$) δ 0.63 (t, 3H), 0.96 (d, 3H), 1.42-1.58 (m, 1H), 1.64-1.76 (m, 1H), 1.78-1.92 (m, 1H), 2.04-2.2 (m, 2H), 2.17 (s, 6H), 2.20-2.28 (m, 1H), 6.56 (m, 1H), 6.56-6.66 (m, 2H), 7.08 (t, 1H); $^{13}$C NMR (CDCl$_3$) δ 12.24, 16.10, 23.91, 36.29, 45.40, 51.43, 64.59, 113.37, 115.70, 119.90, 129.07, 145.64, 156.61.

Example 20

Preparation of (±)-3-(1-(Dimethylamino)-2-methylpentan-3-yl)phenol (mixture of (R,R) and (S,S) stereoisomers) from deprotection of 3-(3-(tert-butyldimethylsilyloxy)phenyl)-N,N,2-trimethylpentan-1-amine Crude 3-(3-(tert-butyldimethylsilyloxy)phenyl)-N,N,2-trimethylpentan-1-amine (6.49 g, 19.3 mmol) was dissolved in MeOH (50 mL) and conc. H$_2$SO$_4$ (2.5 mL, 45.0 mmol).

The clear solution was stirred at room temperature for 5.75 h. The reaction was diluted with water (50 mL) and the MeOH removed. The residue was extracted with CH$_2$Cl$_2$ (50, 30, 20 mL). The aqueous layer was made basic with solid Na$_2$CO$_3$ (5 g) and the resulting oily mixture was extracted with CH$_2$Cl$_2$ (50, 35, 15 mL). The organic extracts were combined, dried over Na$_2$SO$_4$), filtered and evaporated to obtain a viscous colorless oil which was dried under vacuum overnight (3.65 g; 85.3%): m/z 222 (M+1); $^1$H NMR (CDCl$_3$) δ 0.69 (t, 3H), 0.97 (d, 3H), 1.44-1.60 (m, 1H), 1.66-1.78 (m, 1H), 1.80-1.92 (m, 1H), 2.04-2.16 (m, 2H), 2.18 (s, 6H), 2.22-2.32 (m, 1H), 6.57 (t, 1H), 6.62 (m, 1H), 6.65 (m, 1H), 7.11 (t, 1H); $^{13}$C NMR (CDCl$_3$ 36.37, 45.47, 51.46, 64.69, 113.29, 115.67, 129.08, 145.78, 156.48.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preparing a substantially optically pure (R,R) stereoisomer of a compound of formula (V):

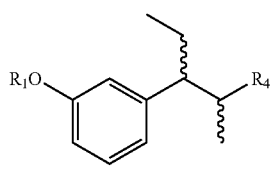

V or a pharmaceutically acceptable salt thereof, the method comprising:

(i) reacting a compound of formula (II):

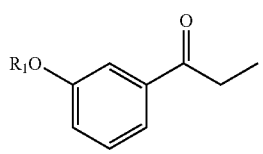

II or a pharmaceutically acceptable salt thereof, with a cyanoethyl phosphonic acid derivative of formula (III):

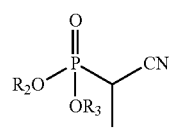

III to produce a mixture comprising the E-isomer and Z-isomer of a compound of formula (I):

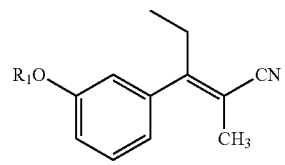

I or a pharmaceutically acceptable salt thereof; and (ii) separating the E-isomer from the Z isomer in the mixture, thereby obtaining a substantially pure E-isomer of the compound of formula (I) or the pharmaceutically acceptable salt thereof;

(iii) reacting the substantially pure E-isomer of the compound of formula (I) or the pharmaceutically acceptable salt thereof with one or more reducing agents, and optionally an alkylating agent, thereby obtaining the compound of formula (V) or the pharmaceutically acceptable salt thereof as a mixture of (R,R) and (S,S) stereoisomers that is substantially free of (R,S) and (S,R) stereoisomers; and (iv) separating the (R,R) stereoisomer from the (S,S) stereoisomer in the mixture, thereby obtaining the substantially optically pure stereoisomer of a compound of formula (V), wherein R$_1$ represents a hydrogen or an aliphatic, aryl, or phenolic oxygen protecting group, each of R2 and R3 independently represents a hydrogen, alkyl or aryl, R$_4$ represents CN or CH$_2$N(R$_5$)$_2$, and R$_5$ represents a hydrogen or alkyl.

2. The method according to claim 1, wherein the (R,R) stereoisomer is separated from the (S, S) stereoisomer by chromatography.

3. The method of claim 2, wherein the chromatography comprises one or more selected from the group consisting of batch chromatography, supercritical fluid chromatography, and continuous chromatography.

4. The method of claim 2, wherein the chromatography comprises a simulated moving bed chromatography.

5. The method according to claim 1, comprising:

(i) reducing the substantially pure E-isomer of the compound of formula (I) or the pharmaceutically acceptable salt thereof to a compound of formula (VI):

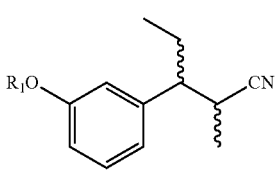

VI or pharmaceutically acceptable salt thereof as a mixture of (R,R) and (S,S) stereoisomers of the compound of formula (VI) that is substantially free of (R,S) and (S,R) stereoisomers of the compound of formula (VI), wherein the reducing step comprises a reaction catalyzed by palladium or platinum on carbon; and (ii) separating the (R,R) stereoisomer from the (S,S) stereoisomer in the mixture, thereby obtaining a substantially optically pure (R,R) stereoisomer of the compound of formula (VI) or a pharmaceutically acceptable salt thereof.

6. The method according to claim 5, further comprising reacting the substantially optically pure (R,R) stereoisomer of the compound of formula (VI) or the pharmaceutically acceptable salt thereof with a reducing agent, and optionally an alkylating agent, thereby obtaining a substantially optically pure (R,R) stereoisomer of a compound of formula (VII):

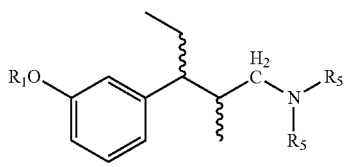

VII or a pharmaceutically acceptable salt thereof.

7. The method according to claim 1, comprising:

(i) reacting the compound of formula (I) or the pharmaceutically acceptable salt thereof with a reducing agent and optionally a alkylating reagent in the presence of a nickel catalyst, thereby obtaining a compound of formula (IV):

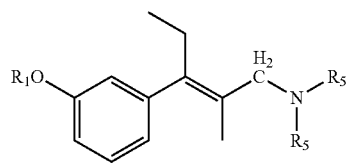

IV or a pharmaceutically acceptable salt thereof; and (ii) reducing the compound of formula (IV) or the pharmaceutically acceptable salt thereof to a compound of formula (VII):

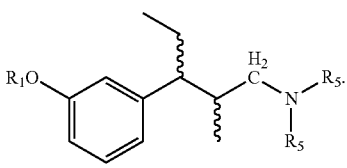

VII or a pharmaceutically acceptable salt thereof as a mixture of (R,R) and (S,S) stereoisomers of the compound of formula (VII) that is substantially free of (R,S) and (S,R) stereoisomers of compound of formula (VII); and (iii) separating the (R,R) stereoisomer from the (S,S) stereoisomer in the mixture, thereby obtaining a substantially optically pure (R,R) stereoisomer of the compound of formula (VII) or pharmaceutically acceptable salt thereof.

8. The method according to claim 1, wherein the substantially pure E-isomer of the compound of formula (I) is obtained by separating the E-isomer from the Z-isomer in the mixture by column chromatography.

9. A method of preparing a substantially optically pure (R,R) stereoisomer of a compound of formula (VII):

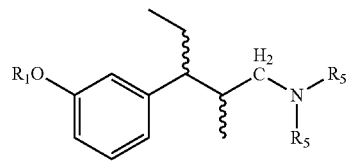

VII or a pharmaceutically acceptable salt thereof, the method comprising:

(i) reacting a compound of formula (II):

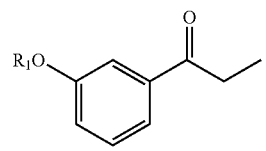

II or a pharmaceutically acceptable salt thereof, with a cyanoethyl phosphonic acid derivative of formula (III):

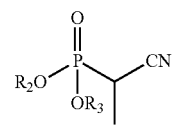

III to produce a mixture comprising the E-isomer and Z-isomer of a compound of formula (I):

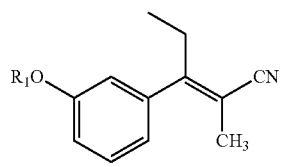

I or a pharmaceutically acceptable salt thereof; and (ii) separating the E-isomer from the Z isomer in the mixture, thereby obtaining a substantially pure E-isomer of the compound of formula (I) or the pharmaceutically acceptable salt thereof;

(iii) reducing the substantially pure E-isomer of the compound of formula (I) or the pharmaceutically acceptable salt thereof, thereby obtaining a compound of formula (VI):

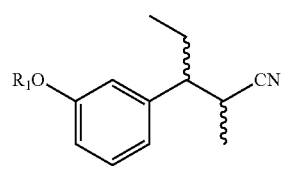

VI or a pharmaceutically acceptable salt thereof as a mixture of (R,R) and (S,S) stereoisomers of the compound of formula (VI) that is substantially free of (R,S) and (S,R) stereoisomers of compound of formula (VI);

(iv) separating the (R,R) stereoisomer from the (S,S) stereoisomer in the mixture, thereby obtaining a substantially optically pure (R,R) stereoisomer of the compound of formula (VI) or the pharmaceutically acceptable salt thereof; and (v) reacting the substantially optically pure (R,R) stereoisomer of the compound of formula (VI) or the pharmaceutically acceptable salt thereof with a reducing agent, and optionally an alkylating agent, thereby obtaining the substantially optically pure (R,R) stereoisomer of compound of formula (VII) or the pharmaceutically acceptable salt thereof, wherein $R_1$ represents a hydrogen or an aliphatic, aryl, or phenolic oxygen protecting group, each of R2 and R3 independently represents a hydrogen, alkyl or aryl, and $R_5$ represents a hydrogen or alkyl.

10. The method according to claim 9, wherein $R_1$ represents a hydrogen, and $R_5$ represents a methyl.

11. The method according to claim 9, wherein the substantially pure E-isomer of the compound of formula (I) is obtained by separating the E-isomer from the Z-isomer in the mixture by column chromatography.

12. A method of preparing a substantially optically pure (R,R) stereoisomer of a compound of formula (VII):

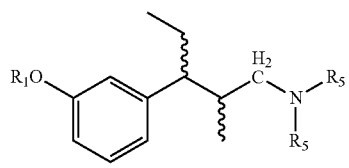

VII or a pharmaceutically acceptable salt thereof, the method comprising:

(i) reacting a compound of formula (II):

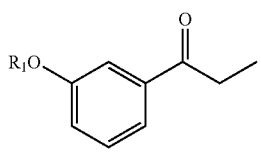

II or a pharmaceutically acceptable salt thereof, with a cyanoethyl phosphonic acid derivative of formula (III):

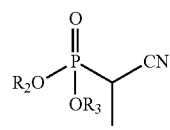

III to produce a mixture comprising the E-isomer and Z-isomer of a compound of formula (I):

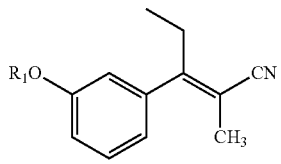

I or a pharmaceutically acceptable salt thereof;

(ii) separating the E-isomer from the Z isomer in the mixture, thereby obtaining a substantially pure E-isomer of the compound of formula (I) or the pharmaceutically acceptable salt thereof;

(iii) reacting the substantially pure E-isomer of the compound of formula (I) or the pharmaceutically acceptable salt thereof with a reducing agent, and optionally an alkylating agent, thereby obtaining a compound of formula (IV):

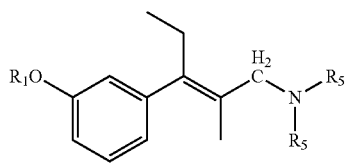

IV or a pharmaceutically acceptable salt thereof;

(iv) reducing the compound of formula (IV) or the pharmaceutically acceptable salt thereof, thereby obtaining the compound of formula (VII) or the pharmaceutically acceptable salt thereof in a mixture of (R,R) and (S,S) stereoisomers that is substantially free of (R,S) and (S,R) stereoisomers; and (v) separating the (R,R) and (S,S) stereoisomers in the mixture, thereby obtaining the substantially optically pure (R,R) stereoisomer of the compound of formula (VII) or a pharmaceutically acceptable salt thereof, wherein $R_1$ represents a hydrogen or an aliphatic, aryl, or phenolic oxygen protecting group, each of R2 and R3 independently represents a hydrogen, alkyl or aryl, and $R_5$ represents a hydrogen or alkyl.

13. The method according to claim 12, wherein $R_1$ represents a hydrogen, and $R_5$ represents a methyl.

14. The method according to claim 12, wherein the substantially pure E-isomer of the compound of formula (I) is obtained by separating the E-isomer from the Z-isomer in the mixture by column chromatography.

15. A method of preparing a substantially optically pure (R,R) stereoisomer of a compound of formula (VII):

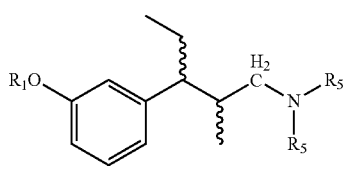

VII or a pharmaceutically acceptable salt thereof, the method comprising:

reacting a compound of formula (II):

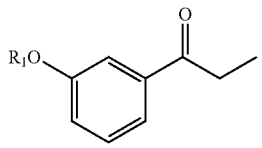

or a pharmaceutically acceptable salt thereof, with a cyanoethyl phosphonic acid derivative of formula (III):

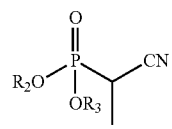

to produce a mixture comprising the E-isomer and Z-isomer of a compound of formula (I):

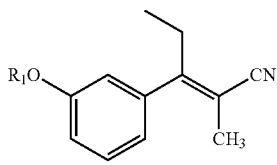

or a pharmaceutically acceptable salt thereof;

(ii) separating the E-isomer from the Z isomer in the mixture, thereby obtaining a substantially pure E-isomer of the compound of formula (I) or the pharmaceutically acceptable salt thereof;

(iii) reacting the substantially pure E-isomer of the compound of formula (I)
or the pharmaceutically acceptable salt thereof with one or more reducing agents, and optionally an alkylating agent, thereby obtaining a compound of formula (VII) or a pharmaceutically acceptable salt thereof in a mixture of (R,R) and (S,S) stereoisomers that is substantially free of (R,S) and (S,R) stereoisomers; and (iii) separating the (R,R) and (S,S) stereoisomers in the mixture, thereby obtaining the substantially optically pure (R,R) stereoisomer of the compound of formula (VII) or the pharmaceutically acceptable salt thereof, wherein $R_1$ represents a hydrogen or an aliphatic, aryl, or phenolic oxygen protecting group, each of R2 and R3 independently represents a hydrogen, alkyl or aryl, and $R_5$ represents a hydrogen or alkyl.

16. The method according to claim 15, wherein $R_1$ represents a hydrogen, and $R_5$ represents a methyl.

17. The method according to claim 15, wherein the wherein the substantially pure E-isomer of the compound of formula (I) is obtained by separating the E-isomer from the Z-isomer in the mixture by column chromatography.

* * * * *